(12) United States Patent
Colister et al.

(10) Patent No.: US 12,367,968 B2
(45) Date of Patent: *Jul. 22, 2025

(54) CONTINUOUS IMPROVEMENT TOOL

(71) Applicant: Talis Clinical LLC, Streetsboro, OH (US)

(72) Inventors: Gary Colister, Hudson, OH (US); Giuseppe Saracino, Gainsville, FL (US); William Murphy, Aurora, OH (US); Harish Lecamwasam, Scottsdale, AZ (US)

(73) Assignee: Talis Clinical LLC, Streetsboro, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/192,430

(22) Filed: Mar. 4, 2021

(65) Prior Publication Data

US 2021/0193308 A1 Jun. 24, 2021

Related U.S. Application Data

(63) Continuation-in-part of application No. 16/239,023, filed on Jan. 3, 2019, now abandoned.
(Continued)

(51) Int. Cl.
G16H 40/20 (2018.01)
G16H 10/60 (2018.01)
G16H 50/70 (2018.01)

(52) U.S. Cl.
CPC ............ *G16H 40/20* (2018.01); *G16H 10/60* (2018.01); *G16H 50/70* (2018.01)

(58) Field of Classification Search
CPC ........ G16H 50/20; G16H 80/00; G16H 10/60; G16H 40/67; A61B 5/7275; A61B 5/0022;
(Continued)

(56) References Cited

U.S. PATENT DOCUMENTS 3,892,171 A 7/1975 Fitch et al.
5,954,666 A 9/1999 Snell
(Continued)

FOREIGN PATENT DOCUMENTS

EP 3839960 6/2021
JP 2004-533662 A 11/2004
(Continued)

*Primary Examiner* — Daniel W Parcher
(74) *Attorney, Agent, or Firm* — McCoy Russell LLP

(57) ABSTRACT

A system for improving patient outcomes, including a data storage and transfer network; a communication hub for collecting data from and transmitting data to, agnostically, electronic devices, for time stamping and storing data, and translating data received and sent; and a rules engine for transmitting data to any number of electronic devices or receiving and sending data via the network, and a user interface rules engine for receiving data and accessing patient medical conditions that provides the user with ability to select any point in time during the patient treatment to review details and create guidance rules so that data can be acquired, consolidated and actionable insights can be delivered in real time; a continuous quality improvement tool engine that provides a user friendly means of defining data search scripts to acquire the required data for analysis.

10 Claims, 14 Drawing Sheets

Related U.S. Application Data

(60) Provisional application No. 62/613,218, filed on Jan. 3, 2018.

(58) Field of Classification Search
CPC ... A61B 5/7282; A61B 5/7465; G06F 3/0482; G06F 3/0484; G06F 16/22; G06F 16/215
See application file for complete search history.

(56) References Cited

U.S. PATENT DOCUMENTS

| | | | |
|---|---|---|---|
| 6,229,536 B1 | 5/2001 | Alexander et al. | |
| 6,364,834 B1 | 4/2002 | Reuss et al. | |
| 6,553,436 B2 | 4/2003 | Ando et al. | |
| 6,559,868 B2 | 5/2003 | Alexander et al. | |
| 7,315,825 B2 | 1/2008 | Rosenfeld | |
| 7,467,093 B1 | 12/2008 | Newton et al. | |
| 8,000,937 B2 | 8/2011 | Zeng et al. | |
| 8,149,131 B2 | 4/2012 | Blomquist | |
| 8,229,760 B2 | 7/2012 | Hasan et al. | |
| 8,291,337 B2 | 10/2012 | Gannin et al. | |
| 8,310,336 B2 | 11/2012 | Muhsin et al. | |
| 8,553,036 B2 | 10/2013 | Taylor et al. | |
| 8,660,860 B2 | 2/2014 | Wehba et al. | |
| 8,674,837 B2 | 3/2014 | Gilham et al. | |
| 8,730,243 B2 | 5/2014 | Wenholz et al. | |
| 8,990,722 B2 | 3/2015 | Gannon et al. | |
| 9,095,274 B2 | 8/2015 | Fein et al. | |
| 9,179,852 B2 | 11/2015 | Audet et al. | |
| 9,393,366 B2 | 7/2016 | Gannon et al. | |
| 9,400,874 B2 | 7/2016 | Powell et al. | |
| 9,927,943 B2 | 3/2018 | Gannon et al. | |
| 10,255,408 B2 | 4/2019 | Blomquist | |
| 10,354,751 B1 | 7/2019 | McNair | |
| 10,657,222 B2 | 5/2020 | Chan et al. | |
| 11,030,872 B2 | 6/2021 | Chan et al. | |
| 11,031,129 B2 | 6/2021 | Zaleski | |
| 11,786,183 B2 | 10/2023 | Kiani et al. | |
| 2004/0015891 A1* | 1/2004 | Arellano-Payne | G06F 16/88 717/137 |
| 2004/0044775 A1* | 3/2004 | Takano | H04L 67/56 709/227 |
| 2004/0054294 A1 | 3/2004 | Ramseth | |
| 2004/0083467 A1* | 4/2004 | Hanley | G06F 8/52 717/148 |
| 2005/0159666 A1 | 7/2005 | Pearce et al. | |
| 2005/0171815 A1 | 8/2005 | Vanderveen | |
| 2006/0071797 A1 | 4/2006 | Rosenfeld et al. | |
| 2007/0179806 A1 | 8/2007 | Knowlton et al. | |
| 2008/0004904 A1 | 1/2008 | Tran | |
| 2008/0097914 A1 | 4/2008 | Dicks et al. | |
| 2008/0316045 A1 | 12/2008 | Sriharto et al. | |
| 2011/0153578 A1* | 6/2011 | Pogodin | G06Q 10/10 707/694 |
| 2011/0227739 A1 | 9/2011 | Gillham et al. | |
| 2012/0035957 A1 | 2/2012 | Hanz et al. | |
| 2012/0075103 A1* | 3/2012 | Powell | G16H 15/00 340/573.1 |
| 2012/0278099 A1* | 11/2012 | Kelly | G16H 10/60 705/2 |
| 2012/0290266 A1* | 11/2012 | Jain | G16H 50/20 702/187 |
| 2014/0046674 A1 | 2/2014 | Rosenfeld et al. | |
| 2014/0142963 A1 | 5/2014 | Hill et al. | |
| 2014/0222446 A1 | 8/2014 | Ash et al. | |
| 2014/0249855 A1 | 9/2014 | Moore | |
| 2014/0266787 A1 | 9/2014 | Tran | |
| 2015/0025329 A1 | 1/2015 | Amarasingham et al. | |
| 2016/0117446 A1* | 4/2016 | Hussam | G16H 80/00 705/3 |
| 2016/0246943 A1 | 8/2016 | Lake et al. | |
| 2017/0140108 A1 | 5/2017 | Lee et al. | |
| 2017/0311904 A1 | 11/2017 | Davis et al. | |
| 2017/0372037 A1 | 12/2017 | Muecke et al. | |
| 2020/0035366 A1 | 1/2020 | Gummireddy et al. | |
| 2020/0227148 A1 | 7/2020 | Cohen et al. | |
| 2020/0359913 A1 | 11/2020 | Ghodrati et al. | |
| 2020/0394334 A1 | 12/2020 | Bulut et al. | |
| 2021/0065889 A1 | 3/2021 | Page | |
| 2021/0077035 A1 | 3/2021 | Kayser et al. | |
| 2021/0141786 A1 | 5/2021 | Gubau i Forné et al. | |
| 2021/0151145 A1 | 5/2021 | Dunn et al. | |
| 2021/0151178 A1 | 5/2021 | Singh et al. | |
| 2021/0202086 A1 | 7/2021 | Cherdak | |
| 2021/0225505 A1 | 7/2021 | Khare et al. | |
| 2021/0233628 A1 | 7/2021 | Rentas et al. | |

FOREIGN PATENT DOCUMENTS

| | | |
|---|---|---|
| JP | 2008204478 A | 9/2008 |
| JP | 2013242745 A | 12/2013 |
| JP | 2015/222588 A | 12/2015 |
| JP | 2016-519806 A | 7/2016 |
| WO | 2021067485 | 4/2021 |
| WO | 2021002847 | 7/2021 |

* cited by examiner

Entry = automated or manual data entry, such as, proactive antibiotic delivery, vital signs, incision time,
Logic path follows for each required entry prompts / notifications.

CONTINUOUS IMPROVEMENT TOOL

CROSS REFERENCE TO RELATED APPLICATIONS

This application is a continuation-in-part of, and claims the benefit of, U.S. patent application Ser. No. 16/239,023, filed Jan. 3, 2019, which is entitled "Continuous Improvement Tool," and is incorporated herein by reference.

BACKGROUND OF THE INVENTION

The present invention is directed to a continuous improvement tool or system, which facilitates the implementation of an effective Continuous Improvement Program.

Medical facilities have an obligation to implement a continuous improvement program focused on improving patient outcomes. A continuous improvement tool must support the medical facility's continuous improvement plan. While there are many reasons for using a continuous improvement tool, Sentinel and Never Events could leverage the capabilities of the continuous improvement tool.

When Sentinel (i.e., an adverse event in health care delivery or other services, which either leads to or has potential to lead to catastrophic outcomes) or Never Events (i.e., a particularly shocking medical error that should never occur) occur, the medical facilities must review the specific conditions leading up to the event and, where possible, take appropriate actions to prevent recurrence. This includes a failure investigation focused on identifying the root cause(s) of the event. It is not uncommon to identify several potential root cause(s).

Effective failure investigation requires the ability to assess the impact of all patient interaction (patient care activities and conditions) and the patient's response. Data available in Electronic Health Records (EHR), by itself, is not adequate to support process control processes. Normally, currently electronic patient records are limited to a series of snap shots in time during patient care. The snap shots routinely do not provide an effective means to assess the patient interactions and response. So, the determination of correlation between any specific patient interaction may be limited by the lack of a number of scientifically significant facts required to make the determination. Additionally, the required failure investigation should be expanded to other patients with similar conditions to better assess and identify any correlation of results in multiple cases, since one data point does not identify a trend. Under the current practice this type of assessment is not meaningful given the limitations of the data available for review.

Effective Continuous Improvement Programs utilize process control tools to collect the information required to drive a continuous spiral of improvement. The base foundation of any process control process used to drive a continuous spiral of improvements is to monitor the process to ensure consistent compliance with the defined protocol. With knowledge that the protocol is consistently followed, data analysis may be used to assess the capabilities of the protocol and its ability to deliver the expected outcomes. There are any number of reasons for using the continuous improvement tool, including, for example, (1) investigation of Sentinel or Never events, (2) review of patient outcomes from previous cases with reviewer defined criteria, (3) monitoring the frequency of deviations to reviewer defined criteria, (4) assessing compliance to patient care protocol requirements, (5) alerting the reviewer of new cases meeting the defined criteria, (6) analysis of real-world data to validate any recommended protocol changes, and the like.

The concept of using traditional process controls tools in the medical treatment of patients is a relatively new concept. Previously, process control tools available for use in the healthcare environment, were considered medical devices. Effective process control systems drive a continuous spiral of improvement as knowledge is gained. This often drives process modifications multiple times a year. As a medical device, these process modifications would require FDA notification prior to release to the market in most cases. This requirement made developing an effective process control system, designed to drive a continuous spiral of patient outcome improvement program, impractical with no business model justifying the cost of continued support as the hospitals gained knowledge.

Adding to the complexities associated with implementing an effective process control tool is that the various sources of data were not capable of being collected and compiled into a singular data set for effective analysis and response to the relevant information. In the absence of an agnostic interface (a system designed to communicate with all required electronic devices providing or receiving data to or from the system), there is no means to collect, translate, store, and transmit all required information. Unless linking all the various sources of data is functional, such a process control tool cannot be effective. Additionally, there is no means to organize the data to provide an accurate representation of the patient's response to patient care interactions. This is the result of both internal clocks of the electronic devices not in agreement with other internal clocks, and/or actual data collection time not being available from the source. In the absence of a means to time-synchronize the data from the various sources, the process control tool cannot effectively provide an accurate representation of what occurred when. The significance of this limitation is obvious when one considers that one of the primary goals of patient care records is to assess the patient's response to specific patient care interactions including but not limited to drug delivery, medical device setting changes, medical practitioner interaction with patient, etc.

Additionally, the frequency of the data provided limited snap shots of the actual patient care and patient response details required to adequately evaluate the patient care history.

Process control engineers routinely use "Design of Experiments" tools to develop and conduct studies. There is no way to conduct experiments on patients with specific values of identified parameters required to be used with a specific patient. An alternative is to use real-world data to retrospectively analyze the data from cases meeting the study's defined parameters.

The data required to develop and conduct these studies using real-world data is not readily retrievable from any one data source within a medical care facility. Additionally, much of the data is minimized by taking snap shots of data, such as wave forms, limited data due to the frequency of data entry during the interaction with the patient, or data stored in electronic systems or medical devices that do not talk to each other.

An effective process control system must address this by collecting the required data and ideally any potentially relevant data available from any electronic device including manual entry of data. The data from the various electronic sources must be stored in a data repository and time synchronized as the data is received. The synchronization is critical because the various electronic devices often have internal clocks. These internal clocks often are not in sync with each other. Therefore, an external synchronization is required to appropriately align the data to the actual time of data collection.

Once the data collection, synchronization, storage, real time process controls, including user prompts and notifications delivered in real time, are in place to manage the active process, the ability to analyze the data and protocol outcome is required to gain knowledge required to improve the process outcomes. This concept is often referred to as continuous improvement. The most basic quality standards require a continuous improvement program. While the hospitals have been required to have continuous improvement tools, as stated previously they have not had access to any process control systems that provide the ability to effectively implement a continuous improvement program.

Proposed modifications to patient care protocols require validation prior to implementation. A continuous improvement tool must provide a means to use real-world data to perform the required validation studies justifying the approval of proposed changes.

Hospitals have the need to minimize the need to write specific search scripts each time a failure investigation or design of experiment studies is needed. Therefore, an effective continuous improvement tool must provide user-friendly search scripts designed for specific protocols including ability to modify the protocol parameters and parameter limits facilitating implementation of an effective continuous improvement program with minimal, if any, additional staff to support the program.

The inability to effectively implement process controls is a significant limitation of both paper and Electronic Health Records (EHR). Medical facilities have the authority to collect quality data not included in the EHR. However, as discussed previously, the data available to populate the quality data was not available. Utilization of the process control tools would provide the Medical Facilities with an ability to maintain and utilized the expanded data scope.

SUMMARY OF THE INVENTION

The continuous improvement tool or system of the present invention is designed to facilitate the analysis of data and support the Quality Improvement Program of the medical facility or system. The present invention as designed is not necessarily a medical device, in that sense, and leverages the facility identified subject matter experts input to configure the invention to the specific needs of each customer, including modifications as new knowledge is gained by the customer.

The continuous improvement tool is designed to interact with a process control system capable of collecting data from various sources, including electronic sources including medical devices, lab records, patient care records, image records, etc. The process control system stores not only the data required for the patient care records but also any number of parameters identified as quality data, as currently provided by the Interoperability Environment system.

The continuous improvement tool of the present invention allows analysis of historical and future cases meeting the criteria defined by the potential actions to be considered. Therefore, the tool provides a means to effectively assess the impact of the changes. Without the tool, a commonly accepted process control would be to use design of experiment tools in controlled studies. With the tools the required analysis rapidly provides knowledge available from historical cases. Additionally, if there are any new cases meeting the criteria, the reviewer may be notified of the new case.

The continuous improvement tool of the present invention provides means to access and assess the data for specific cases, and access and assess other cases with the reviewer's identified and defined conditions from historical records or future records as they occur. The availability of process control tools has not been available to Medical Facilities. These tools have the ability to collect and store data from any electronic source including manually entered data. The data stored may include data required to populate Electronic Health Records as well as quality data collected but not contained in the EHR.

The present invention is directed to a continuous improvement system and method to operationalize process controls for patient care protocols to improve patient outcomes; designing and conducting various studies requiring actual patient care data including but not limited to expanded failure investigation of Never events by including multiple patients care records with user defined criteria, including design of retrospective studies using real-world data, including validation of proposed patient care protocols, white papers and peer review articles using real-world data, and utilizing real-world data to supplement or replace the needs for traditional clinical studies, and creation of quality metrics with the ability to monitor performance to the metrics, including percentage compliance to protocols, frequency of patient care transfer within a single patient care protocol, initial patient outcome, patient outcome within 90 days of treatment, care area utilization, and so on.

The present invention includes a patient database containing information concerning the medical condition, history, and status of each of the patients, but the system also includes real-world data. Real-world data are the data relating to patient health status and/or the delivery of health care routinely collected from a variety of sources and can come from a number of sources, such as for example, Electronic health records (EHRs), claims and billing activities, product and disease registries, patient-generated data including in home-use settings, and data gathered from other sources that can inform on health status, such as mobile devices.

The present invention includes a patient database; at least one communication hub comprising a rules engine for collecting and time synchronizing data from any number of electronic devices, including medical devices and manual entries; and a user interface rules engine for receiving and storing monitored data elements from patients and accessing patient data elements indicative of a medical condition associated with each of the patients, for transmitting data to any number of electronic devices, including medical devices, in a format acceptable to the electronic device, including continuous wave form data as provided by the medical device, collected during the treatment of the patient, and quality data not included in any patient record storage location; where the continuous improvement system of the present invention provides a user with ability to select any point in time during the patient treatment to:
  i. review the details collected regarding the treatment at the selected time
  ii. review the details before or after the selected time.
  iii. create guidance rules to identify cases identified as complying with the defined rules, the user may define the period of time used to identify the cases for review, the user may select future cases, or past cases, or a combination of the two.
  iv. define who, when and how to communicate that cases meeting the defined criteria are available for review, in this case the who may be only the individual(s) evaluating the defined criteria without notification to anyone monitoring a current case, or including specific individuals monitoring the current case;

where the user interface rules engine can collect, store and process data in real time, compose views that organize data for end-users to consume, let a user create execution steps on the data streams, to notify end-users based on execution steps defined by end-users, to display an organized view of data within a timeline of events, for end-users to change or augment the execution steps, and provide notifications at the same time the end-user is reviewing data.

DESCRIPTION OF THE DRAWINGS

The foregoing and other features and advantages of the present invention will become apparent to those skilled in the art to which the present invention relates upon reading the following description with reference to the accompanying drawings, in which.

DETAILED DESCRIPTION OF THE INVENTION

Figure 1:
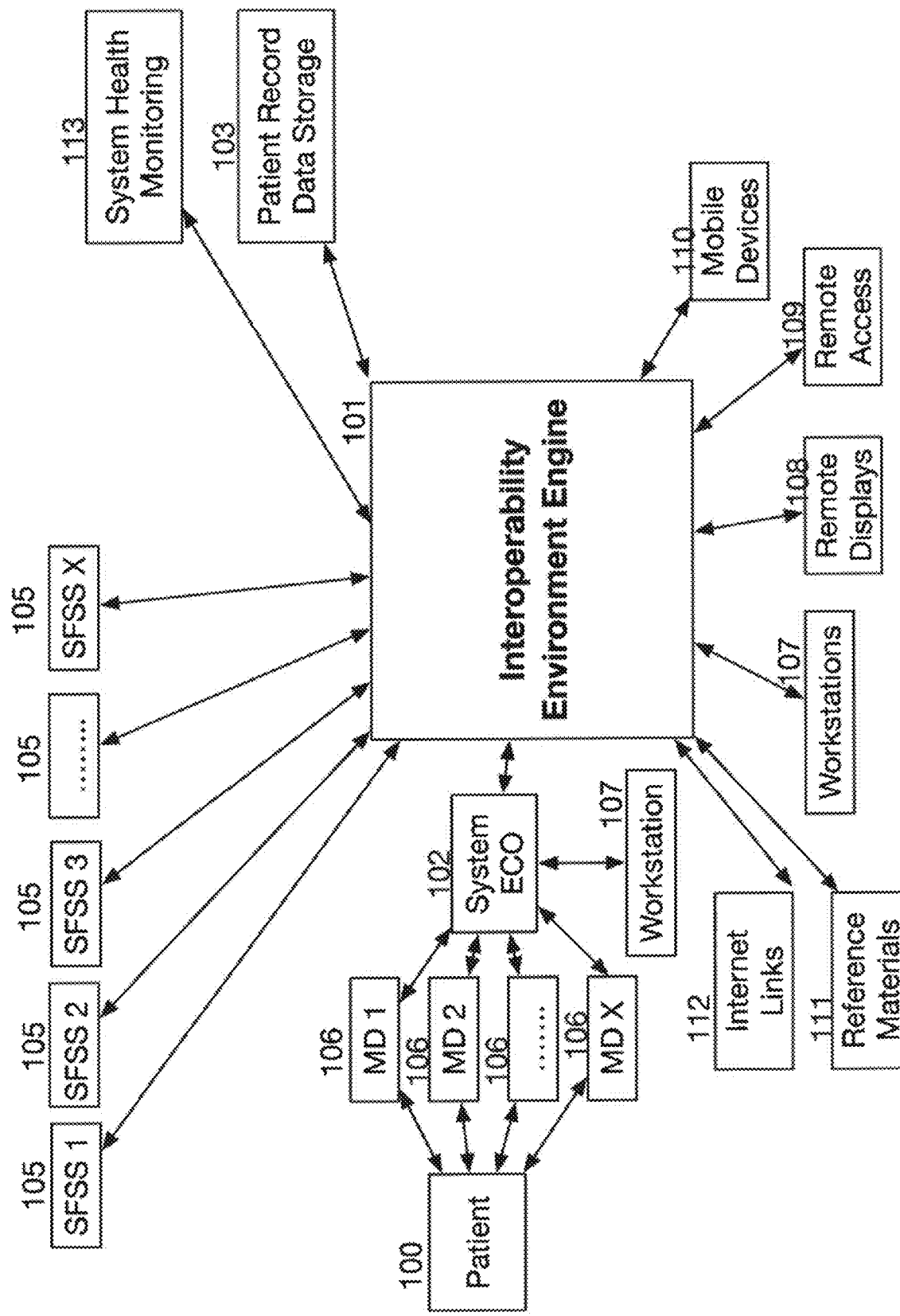
FIG. 1 is a flow diagram of a global view of an Interoperability Environment showing the various communication sources and targets.

The present invention is directed to a continuous improvement system and method for medical patients to improve patient outcomes which includes a user interface rules engine; at least one monitoring station comprising monitoring equipment where the monitoring equipment includes rules engine for monitoring data elements and for sending the monitored data elements via data transfer network and user interface portal, and includes rules engine for receiving monitored data elements from patients and accessing patient data elements indicative of medical conditions associated with each of the patients; a patient database containing information concerning the medical condition, history, and status of each of the patients; at least one communication hub comprising a rules engine for collecting data from any number of electronic devices including medical devices, using rules engines designed for specific electronic devices, and rules engines for transmitting data from any number of electronic devices including medical devices as well as rules engine for storing data associated with the patient records and/or data to be stored as quality data; a data storage engine comprising a means for collecting data from any number of electronic devices including medical devices and a rules engine for transmitting data to any number of electronic devices including medical devices using rules engines designed for specific devices, as well as rules engine for storing data associated with the patient records and/or data to be stored as quality data; the user interface rules engine providing authorized access to all data, including continuous wave form data, collected during the treatment of the patient and quality data not included in any patient record storage location; and a user interface rules engine that provides the user with ability to select any point in time during the patient treatment to:

i. review the details collected regarding the treatment at the selected time.

ii. review the details before or after the selected time.

iii. create guidance rules to identify cases identified as complying with the defined rules, the user may define the period of time used to search for and identify the cases for review, the user may select future cases only, or past cases to some a defined date, or a combination of the two.

iv. define who, when and how to communicate that cases meeting the defined criteria are available for review, in this case the who may be only the individual(s) evaluating the defined criteria without notification to anyone monitoring a current case, or including specific individuals monitoring the current case.

The user interface rules engine includes means to collect, store and process data in real time, to compose views that organize data for end-users to consume, to let users create execution steps on the data streams, to notify end-users based on execution steps defined by end-users, to display an organized view of data within a timeline of events, for end-users to change or augment the execution steps, and to provide notifications at the same time the end-user is reviewing data. The data storage can be local and/or remote, such as a cloud-based system. By using an appropriately programed computer, data from multiple disparate sources can be acquired, time stamped, and consolidated within a unified view, and process controls and workflows can be run, and actionable insights can be delivered to specific users in real time.

The continuous improvement system of the present invention is supported by the user interface rules engine and provides means to utilize patient care protocol specific data search script templates, which are similar to the workflow screens used during patient care, to facilitate the acquisition of the required data, this minimizes the need for data management experts required to create and run requested data retrieval, retrospectively review data against defined criteria using protocol specific search scripts, expand failure investigation of Never events by including multiple patient care records with user defined criteria, design and conduct retrospective studies using real-world data, including validation of proposed patient care protocols, design of white papers and peer review articles using real-world data, and utilizing real-world data to supplement or replace the needs for traditional clinical studies, create quality metrics with the ability to monitor performance to the metrics, including percentage compliance to protocols, frequency of patient care transfer within a single patient care protocol, initial patient outcome, patient outcome within 90 days of treatment, and care area utilization, and the like, and analyze patient outcomes based on patient care history based on actual visits to the facility and follow-up visits expanded failure investigation of Never events by including multiple patients care records with user defined criteria.

The protocol specific data search templates replace the traditional user interface with database specialists required to write complicated search scripts as requested by the users. As the users analyze the results of the search results, it is not uncommon to request multiple variations to the search criteria. Each time requiring the services of the database specialists based on their assigned priorities. Because of the data required to comply with the search request is stored in multiple formats and sources, multiple database specialists may be required for each search request. The present invention stores all potentially relevant data as patient record data and/or quality data. The system provides access to all potentially relevant data, using the protocol specific search script templates. The use of the protocol specific search script templates eliminates the need for a database specialist's involvement. Instead, the user accesses the appropriate protocol specific search script via the user interface rules engine. The user then populates the template in the same manner that the user used to define the specific protocol requirements. The search criteria may include any data stored as part of the patient record and/or any data stored as quality data, including but not limited to specific cases, patient outcome, patient readmissions, practitioners assigned to the patient treatment, protocol compliance, patient response to patient interaction, notifications, alerts, etc. The benefit being that the user interface rules engine leverages the format most familiar to the user to facilitate the user while defining complicated search requests of data stored in a manner providing a means to access all potentially relevant data.

The acquisition, consolidation, and synchronization of data from multiple disparate sources, into a unified view, facilitates the running of process controls and workflows, and delivering actionable insights to specific users in real time, i.e., the actual time during which an event occurs. Since data is being acquired in real time, the time synchronization is required to accurately align the data from the various sources of information. The internal clocks of the various sources are not in agreement and may not be provided as part of the data provided by the device. Therefore, the data is synchronized to the time collected rather than use the various electronic source times, if available. This allows the data from multiple sources to be presented on the same screen. This allows for an accurate representation and display of the alignment of patient interaction with the patient's response, which is required for an informed assessment of patient response to patient care activities. The identification of which information is actionable is based on user criteria using decision support algorithms and management software. Actionable information can be presented with rich context compared to typical isolated ancillary systems. The information can be personalized to patient, clinical and/or admin user. Users can replay the timeline of events with all relevant information under a given context. Information can be added or deleted to sharpen context, to gain additional knowledge, or to immediately implement changes based on the review.

The novel continuous quality improvement tool enables collection, storage, and automation of process controls and/or workflows on vast disparate data streams that normally are not accessible with paper records or poorly accessible due to isolated ancillary data systems with current electronic systems. Workflow automation changes and data points collected can be easily augmented. The improvement tool of the present invention gives users unique ability to dynamically organize data into views of patient populations regardless of geographic location, with additional ability to pare view according to user specified criteria and the ability to collect data from devices, HIT systems, external sources, user input, or any other source of data which can be made available in electronic format.

The data entry can be a mix of automated and user input. The present invention has the ability to use any of the above to create a set of evaluations on the data stream to trigger notifications intended to notify about deviations from expected workflow, process control or clinical course, as well as the ability to review and replay the sequence of data points in the past so that users can engage in a critical evaluation of a specific event or sequence of events that led to a negative clinical outcome, or non-compliance with or failure of a process control or workflow.

The present invention has the ability to use historical data to generate guidances to manage clinical conditions or new process controls/workflows in real time and the ability for a user to acknowledge that a clinical guidance was true/valid in real time.

The present invention has the ability to change execution pathway per user criteria depending on inputs in real time (e.g. data from a micro assessment could change the frequency of future assessments etc.), as well as enable end-users who are consuming the notifications of the improvement tool to direct and coordinate the team to change the input provided to the improvement tool at the time of the review of data so that the any updated workflow, for instance with additional evaluations, or modified evaluations.

The present invention has the ability to collect, store, and process data in real time. It can compose views that organize data for end-users to consume, to let the user create execution steps on the data streams, to notify end-users based on execution steps defined by end-users, and to present an organized view of data within a timeline of events. Further, the present invention has the ability for end-users to change or augment the execution steps and notifications at the same time the end-user is reviewing data.

The interface rules engine creates guidance rules once the end-user defines the criteria to be evaluated and the notifications that need to be delivered to the care team. End-user can define criteria based on any data-point available in the collected data stream, e.g., from medical devices. Users can be clustered into groups. Patients can be clustered into groups. Patients can be "tagged" with user-defined criteria. Patients can be stratified according to user-defined criteria in real time. An end user on the fly can alter certain thresholds.

When and how communications are made regarding cases meeting defined criteria that need review occur when authorized End-users who use the "continuous improvement tool" have the ability to define the communication type (for instance, email notification to Cockpit user, sms, and who receives it. Also, when they receive it. Communication will be delivered on any device as prescribed by authorized end user in order to optimally support defined workflow. End-user also can configure the escalation process to execute if the notification is not acknowledged or addressed. End users will have ability to "snooze" certain communications if allowed by authorized end user.

The presently claimed invention is directed to a system and device for providing active care for a patient. The presently claimed invention is robust enough that it can locate the application and data storage remote of the facility IT network. Local data storage is limited to temporary data presence to protect against local network failures. Temporary storage during transport of data from the various sources of truth including medical devices. All data, displayed for practitioner use, can be stored, analyzed and processed remote of the facility IT network. The presently claimed invention is not limited to any defined environment or type of facility. The present invention is a real time tool providing Clinical Decision Support to any number of medical practitioners based on the role assigned to the individual practitioner.

The presently claimed invention can receive, store, transmit and display data including wave forms as provided by the medical device or other sources of truth. The wave forms can be created by the medical devices or provided by other sources of truth. The calculation and creation of the wave form is not required.

The present invention is to a real-time update providing real time details required for the practitioner to assess specific patient conditions and when appropriate, adjust scheduled activities as dictated by real time patient data including historical data, data collected from vital sign monitors and medical devices delivering patient treatment or data collected by practitioner selected time(s). The tool also allows the practitioner to select specific times to review patient response to interactions with the patient.

Improvement is achieved every time end-users realize that there is a difference between the process followed by end-users and a better process that they could have followed based on best practices, peer-review publications or reviews of data collected and stored by the continuous improvement tool. Errors and negative events will be identified dynamically. When this happens retrospectively, all data will be available (including waveforms and images) to enable the richest possible clinical review. New guidances can be created in real time if specific sentinel events or sequence of data are identified. Deviations from an expected process or workflow can be identified in real time. Following evaluation, any changes to a process control or workflow can be implemented dynamically The following terms used in the description that follows. The definitions are provided for clarity of understanding:

Assessment data is all data relevant to the health of a patient.

A "healthcare location" is a facility, whether temporary or permanent, that is not generally equipped to provide expert medical care on a twenty-four basis. By way of illustration and not as a limitation, a healthcare location may be a remote clinic, a doctor's office, a field hospital, a disaster aid station, a patient transport vehicle and similar care facilities A Caregiver is an individual providing care to a patient. Examples include a nurse, a doctor, medical specialist (for example and without limitation an intensivist, cardiologist or other similar medical specialist).

Clinical data is data relating to the observed symptoms of a medical condition.

Data is all inclusive, including but not limited to, alpha numeric data, wave forms, images, video, photos, pdf documents, A Monitored patient is a person admitted to a healthcare location.

Monitored data is data received from monitoring devices connected to a monitored patient from whom monitored data is collected and whose condition is subject to continuous real time assessment by the medical practitioner actively involved in the patient care or authorized individuals authorized to remotely monitor data (authorized providers). Data manually entered is included as monitored data. All monitored data provided by medical devices is data provided after the medical device completes the active monitoring function of the medical device. For example: U.S. Pat. No. 9,400,874 to Powell et al. and US Publication 2009/0070054 by Zeng et al. describe how to generate a wave form. The wave forms are generated by the medical device and then collected from the medical device and transferred to data storage.

Patient data is data relating to a patient's diagnosis, prescriptions, history, condition, laboratory results and other health-relevant data.

Physiological data is any data relating to the functions of the human body and its processes.

Symptom is any sign or indication of a health condition that can be identified from patient reports and/or assessment data.

The present invention is directed to a continuous improvement system for medical patients which includes a data transfer network, comprising at least one ECO system or communication hub, which comprising a rules engine for collecting and translating data from any number of electronic devices including medical devices and a rules engine for transmitting data to any number of electronic devices including medical devices, as well as a rules engine for storing data associated with the patient records and/or data to be stored as quality data, a patient database containing information concerning the medical condition, history, and status of each of the patients, a data storage engine comprising a means for collecting data from any number of electronic devices including medical devices and a rules engine for translating and transmitting data to any number of electronic devices including medical devices, as well as a rules engine for storing data associated with the patient records and/or data to be stored as quality data, at least one communication hub comprising a rules engine for collecting and translating data from any number of electronic devices including medical devices and rules engine for translating and transmitting data to any number of electronic devices including medical devices, as well as a rules engine for storing data associated with the patient records and/or data to be stored as quality data, where the user interface rules engine that provides access to all data, including continuous wave form data, collected during the treatment of the patient including quality data not included in any patient record storage location, and a user interface rules engine that provides the user with ability to select any point in time during the patient treatment to facilitate review the details collected regarding the treatment that the selected time, review the details before or after the selected time, creating guidance rules to identify cases identified as complying with the defined rules, the user may define the period of time used to identify the cases for review, the user may select future cases only, or past cases to some defined date, or a combination of the two, and to define who, when and how to communicate that cases meeting the defined criteria are available for review, in this case the who may be only the individual(s) evaluating the defined criteria without notification to anyone monitoring a current case, or including specific individuals monitoring the current case.

The present invention uses a data transfer network and a user interface rules engine to facilitate rules-based care of patients receiving care in a healthcare location. A patient may be selected for monitoring based on criteria established by the treatment facility. By way of illustration and not as a limitation, a "monitored patient" comprises a critically ill patient, an acutely ill patient, a patient with a specific illness, a patient with serious injuries, and a patient with an uncertain diagnosis.

A communication hub acquires and time stamps monitored data elements from any electronic device, including medical devices monitoring and/or treating a patient, and translates and transmits the monitoring data over a network to a storage location to be processed by the interoperability environment engine, which is essentially the user interface rules engine. Monitored data comprises physiological data elements, video data elements, and audio data elements. The data collected is synchronized using the time of data collection, i.e., the time stamped monitored data elements. Even if the data already has some sort of time stamp, a time stamp is applied because the data collection time synchronization is required to eliminate the need to collect the internal clock times of the electronic devices providing the data. This is critical because the internal clocks of the electronic devices are not always synchronized with each other. The system communicates, agnostically, with any electronic device including medical devices and manually entered data. The system identifies which information is actionable using an algorithm based upon user criteria.

Time stamping software for time stamping data is known in the art and can be employed for such purpose. In the present invention, the data is time stamped, as the data is collected and stored in the communication hub. Time stamping prior to storage provides a means to ensure that the data collection time is maintained if the data cannot be transferred to the data storage. Since all communication hubs are time synchronized, regardless of the data source, the time of data collection is used to organize the data within the data repository. Therefore, time stamping of the data provides a means to overlap the data providing an accurate representation of the various patient care interactions and the patient response to these interactions. This provides the process of time stamping for each source of data as it is collected agnostically from the device is unique to the ECO system today.

In the present invention, a monitored patient care system provides care to monitored patients based on the capabilities of the healthcare location. The rules engine, the decision support algorithms, the order writing software facilities, and the continued care software are adapted to the capabilities of the healthcare location based on the application of site assessment rules to the healthcare location. In the present invention, components of a healthcare location patient care system may be supplied to the healthcare location to improve the level of its treatment capabilities. The system can replay the timeline of events with all relevant information under a given context and information can be added or deleted to sharpen context, to gain additional knowledge, and to immediately implement changes based upon the review.

The present invention operates in the context of an Interoperability Environment which includes a hardware eco system comprising a rules engines to collect data from any electronic device including medical devices, translate the data from the source electronic device language to the data storage language, translate the data from the data storage language to the language of the target electronic device (any electronic device may be either a source device, a target device or both), store and send electronic data to the core software engine for any electronic source via communication methods, a core software engine having means to collect and transfer electronic data from any number of sources including medical devices, clinical information systems, hospital information systems, a rules engine to apply rules to improve compliance with hospital approved protocols, standards and guidances, a rules engine to apply rules to update all subsystems using any given parameter when the parameter is updated in the official recognized source of truth for that parameter, a rules engine to apply rules to populate the computer information system (or CIS) with all required patient information, a rules engine to apply the rules to maintain all quality and process control data in a format supporting advanced analytics separate from the CIS data, a rules engine to provide a means to communicate notifications to any number of remote electronic devices without limitation of platform, rules engines to support data analysis including failure investigation and process control and machine learning tools, rules engines providing a means to improve adherence to medical practitioner directed patient care, and rules engine to provide two-way communication with electronic devices including medical devices.

The ECO system hardware acquires data elements from medical devices including patient monitors and transmits the data over a network to data storage, identified targets, individuals requiring notification, remote dashboards, remote mobile communication devices, remote monitoring locations. The collected data comprises physiological data elements, video data elements, audio data elements, manually entered patient evaluations, drug delivery, incision time and location, blood product delivery, lab results, admitting evaluation results, post-operative assessments, I/O data, etc. The Interoperability Environment also accesses other data relating to the condition of a patient. By way of illustration and not as limitation, the Interoperability Environment has access to data relating to personal information about the patient, medical history (illnesses, injuries, surgeries, allergies, medications, etc.), admissions information (symptoms, physiological data, time of admission, observations of admitting caregiver), treatment, lab data, test reports (radiology reports and microbiology reports for example), physician's notes, a patient's diagnosis, prescriptions, history, condition, laboratory results and other health-relevant data (collectively "patient data") to the extent available from the healthcare IT network. The data collected over the network, that is, the monitoring data and the patient data, is collectively referred to as "assessment data."

A preferred system utilizes an agnostic approach to communications between data sources and data targets. By agnostic, it is meant that the data is collected from various sources, equipment, instruments, and/or sensors without regard to the language in which it is transmitted, and/or is generalized so that it is interoperable among various systems. So, the system of the present invention does not require a match with the data source to be functional and can accommodate various data sources. The present invention is agnostic in that it is compatible with different devices and/or operating systems. This compatibility is achieved via a communication hub which communicates to any number of electronic devices rules engine using any number of communication protocols developed for specific electronic devices. The communication hub includes a means for translating data received from any electronic source to the data storage language and, in turn, translating from the data storage to the language of the receiving electronic source.

This allows the hospital to utilize any number of suppliers and/or device models within the interoperability environment. This eliminates the need to buy new equipment just to achieve interoperability. The system will allow access to all relevant patient data from all applicable sources as discussed above and a means to store accurately, timely and completely all relevant data regarding patient care and patient response/outcome.

As an example, data can be expressed in many machine-language instructions. Since there are many machine-languages, as is known in the art, each device and operating system functions in its chosen machine-language. The present invention senses the machine-language in which the data is presented and translates it into the machine-language employed by the present invention. The machine-language employed by the present invention is not critical and is one known in the art. So, it is only a matter of translating the machine-language of the data received to that which will function in the method and system of the present invention. In turn, when data is transmitted to an electronic source, it is translated into the machine-language of that source.

Figure 12:
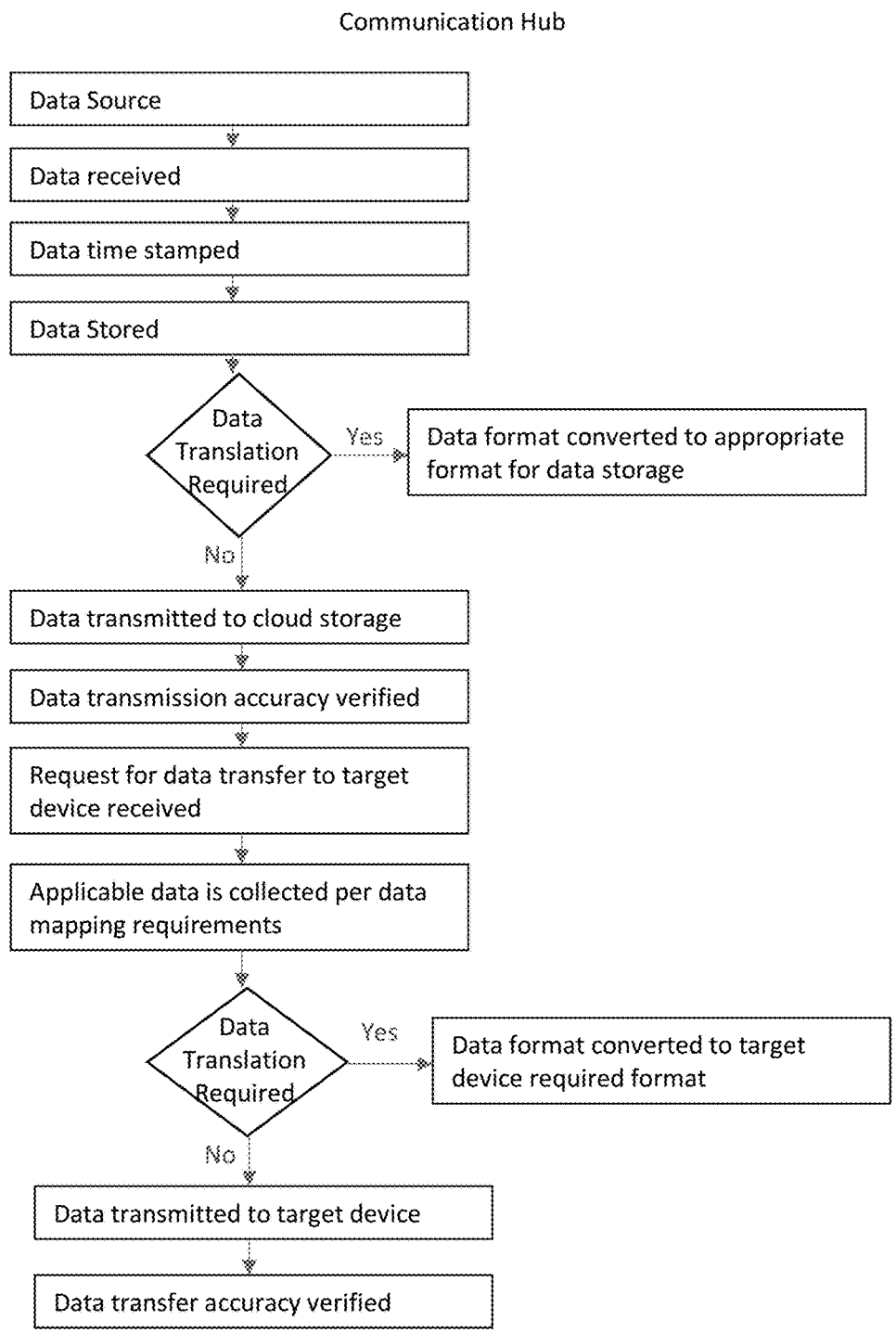
FIG. 12 is a flow diagram of the communications hub or the continuous improvement system of the present invention.

As can be seen in FIG. 12, data from various sources, including monitored data elements from any electronic device, such as medical devices for monitoring and/or treating a patient, and which is essential for the user interface rules engine, is received. Monitored data can comprise physiological data elements, video data elements, and audio data elements. Once the data is received, it is date stamped, and stored. The data which needs to be translated or converted to the machine-language of the communications hub of the present invention, is translated. If translation is unnecessary, the data is stored, preferably in a cloud storage, which provides remote access to the data. The data is then evaluated for the accuracy of the data and that is verified. In response to a request for data transfer to a target device, the applicable data is collected per the data mapping requirements. If data translation is needed for the target device, evaluation and translation are done. Then, the data is transmitted to the target device and the accuracy is verified.

The commonly accepted approach focuses on identifying the means to allow the patient monitoring medical devices to communicate with the medical devices providing patient therapy to appropriately adjust the therapy being provided. Current systems assume that only vital signs collected at the point of care are required to provide clinically proven algorisms all the information required to make the appropriate decision to adjust the medical device provided therapy, which limits the full potential of a device interoperability infrastructure. The present invention expands the capabilities of the system to include all available, but not limited to, medical devices, patient specific details that are applicable to developing and controlling the optimum patient care outcome.

Figure 14:
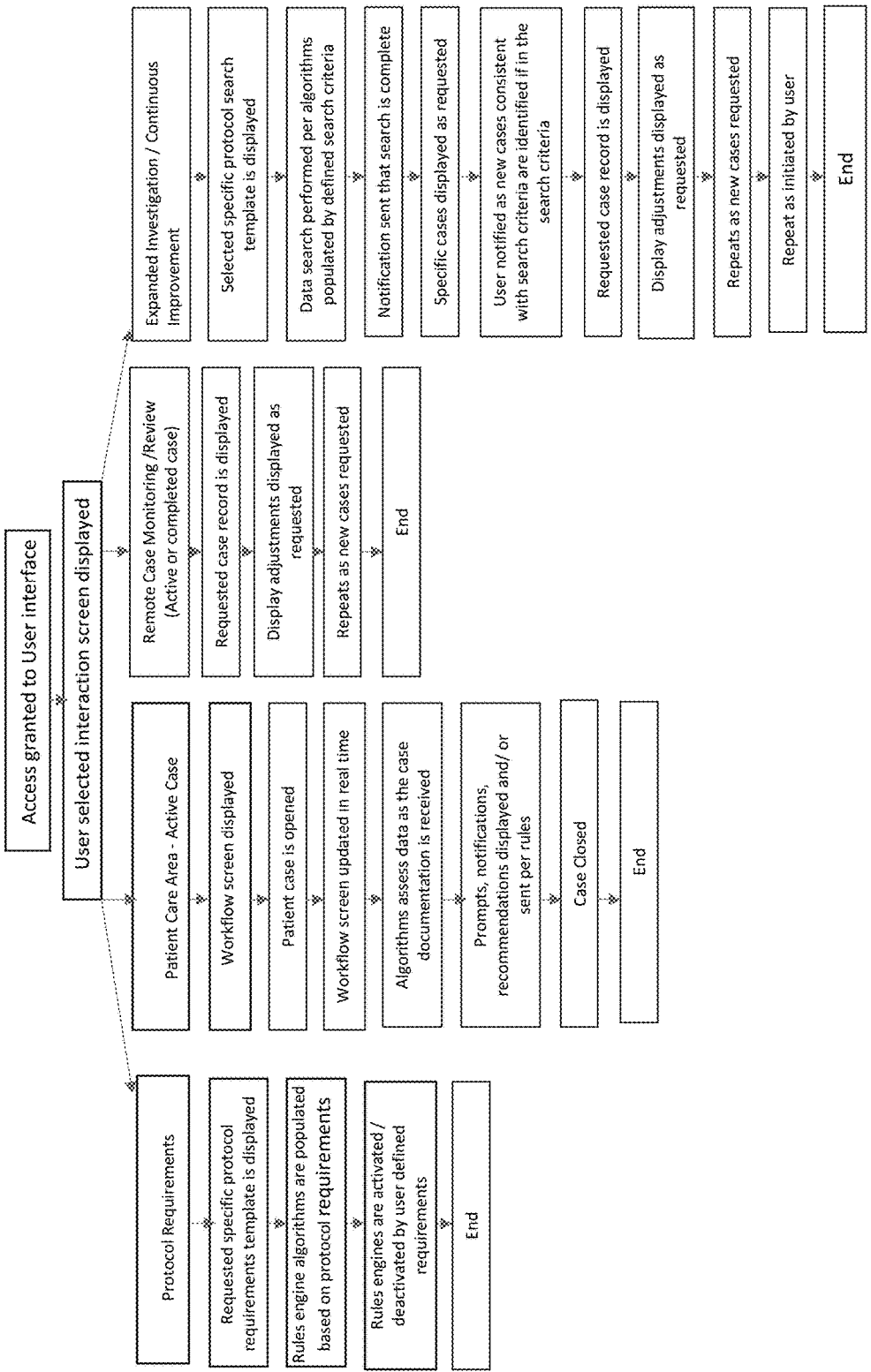
FIG. 14 is a flow diagram of the user interface rules engine of the continuous improvement system of the present invention.

FIG. 14 is a flow diagram illustrating the use of the user interface rules engine. A user may enter and exit the user interface as they want. Once a user is granted access, a user selected interaction screen is displayed. These can include protocol requirements, patient care for an active case, remote case monitoring or review of an active or completed case, or an expanded investigation or continued improvement investigation. Noted below are examples of the user completing specific activities before logging out and then logging in the next activity. Only system activities are included. A user initiates an action prior to the system responding.

Example 1, to Review or Create Protocol Requirements

User interface access is granted
Requested specific protocol requirements template is displayed
Rules engine algorithms are populated based on protocol requirements
Rules engines are activated or deactivated by user defined requirements
The process is Ended.

Example 2, a Case Process

User interface access granted
Workflow screen displayed
Patient case is opened
Workflow screen updated in real time
Algorithms assess data as the case as documentation is received
Prompts, notifications, recommendations displayed or sent
Case closes
End.

Example 3, Case Review (Active or Completed)

User interface access granted
Requested case record is displayed
Display adjustments displayed as requested
End.

Example 4, Expanded Investigation/Continuous Improvement (after Initial Case Review)

User interface access granted
Selected specific protocol search template is displayed
Data search performed per algorithms populated by defined search criteria
Notification sent that search is complete
Specific cases displayed as requested
User notified as new cases consistent with search criteria are identified if in the search criteria
See Case Review
Repeat as initiated by user.

An interoperability environment is represented in FIG. 1, which is a block diagram of the global Interoperability Environment. At the center of FIG. 1 is the Interoperability Environment Engine 101, referred to as the engine. This is to symbolize that it is the core communication tool to ensure timely and accurate communication between the various sources and targets of the data being collected and shared in the global environment. As noted by the two-way arrows, the present invention also supports communication between any number of locations with connections to the Interoperability engine.

The Interoperability Environment is also composed of an ECO system 102. The ECO System is composed of any number of hardware options, utilizing various operating systems such as Linux, Windows, and MacOS. The ECO system resides in close proximity of the electronic devices, including electronic medical devices (or EMD) 106, talking with the ECO System, via any number of communication channels including LAN, Serial, Wi Fi, wireless, etc. The ECO system is utilized as the conduit between the medical devices and the engine to collect, translate and transfer electronic data to the engine for processing to the proper storage locations or specific data targets.

The Interoperability Environment Engine includes a data storage engine and has one or more data repositories to store all data collected prior to sending the data to any target location. For example, the data can come from the patient 100, electronic medical devices 106, workstations 107, patient record data storage 103, remote displays 108, remote access devices 109, mobile devices 110, reference materials 111, internet links 112, and the like. The data storage engine is a software module that a database management system uses to create, read, and update data from a database. The engine tracks each data field based on a start date and end date of the parameter being collected. When combined with the engine time stamping and data collecting, the Interoperability Environment is capable of supporting data analysis of individual parameters as well as interactions with other parameters. Patient Record Data Storage 103 contains all required patient care data collected and stored by the engine.

The data storage engine can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language.

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Computer readable media for embodying computer program instructions and data include all forms of non-volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in special purpose logic circuitry. Any of the foregoing can be supplemented by, or incorporated in, ASICs (application-specific integrated circuits).

The Interoperability Environment Engine or user interface rules engine also is a software module that applies a rule or rule set to the data elements selected from the assessment data from each monitored patient to determine whether the rule for that site has been contravened. In the event the rule has been contravened, an alert to identified authorized practitioners is triggered.

A patient rules generator is part of the user interface rules engine and establishes one or more rules for the monitored patient associated with a patient monitoring station. The patient rules generator collects rules performance measures indicative of the ability of the rule to predict changes in the condition of a patient and uses these measures to assess the efficacy of the rule. The patient rules generator may update a rule, determine that a rule is acceptable as is, or determine that there is insufficient data to revise a rule.

The patient rules generator may also evaluate the assessment data of patients with similar conditions to determine whether a predictive rule can be written and applied to patients with the same or similar conditions. The patient rules generator may also test a proposed rule against historical data to determine whether the rule is predictive of a change in a patient's condition. The patient rules generator generates a rule that is consistent with the service level measures established by a site assessment module.

The patient rules generator is a means to let a user create or define protocol requirements including required protocol execution steps, defined protocol control points, protocol documentation, defined reports, remote access to real time data during active cases or historical records with regard to the collected data.

The user interface rules engine provides the user to access various functions within the system. These functions include, but are not limited to, creation of protocol rules, documentation of patient care plan, documentation of active patient care, remote supervision and monitoring of active cases, review of specific patient care records, creation of data search criteria, access to search results.

Creation of protocol rules provides a means to define the execution steps and process control limits of specific protocols by using a defined protocol template to implement or modify the defined protocol requirements. The requirements will be used to assess an active case against the requirements and provide notifications to all identified individuals in real time. As an example, the anesthesia protocol may require pre-anesthesia evaluation, this evaluation must be completed before moving to the next step, positive patient identification and assigned OR, which is required to electronically verify the proper patient is being moved into the OR, verification of required blood products availability, the blood products must be available prior to starting the procedure, delivery of antibiotic prior to incision, as required by facility protocol, defined acceptable ranges for patient vital signs as generated by the patient monitors are consistently met, delivery of antibiotics during the case, as defined by the facility or patient care plan, documentation of drug deliveries, time of incision, notification to assigned team members, etc. The rules engine algorithm compares the documentation within the case to the protocol requirements, determines the correct notification and prompt, and provides these to the appropriate individuals assigned to the case or supervision of the case.

Figure 13:
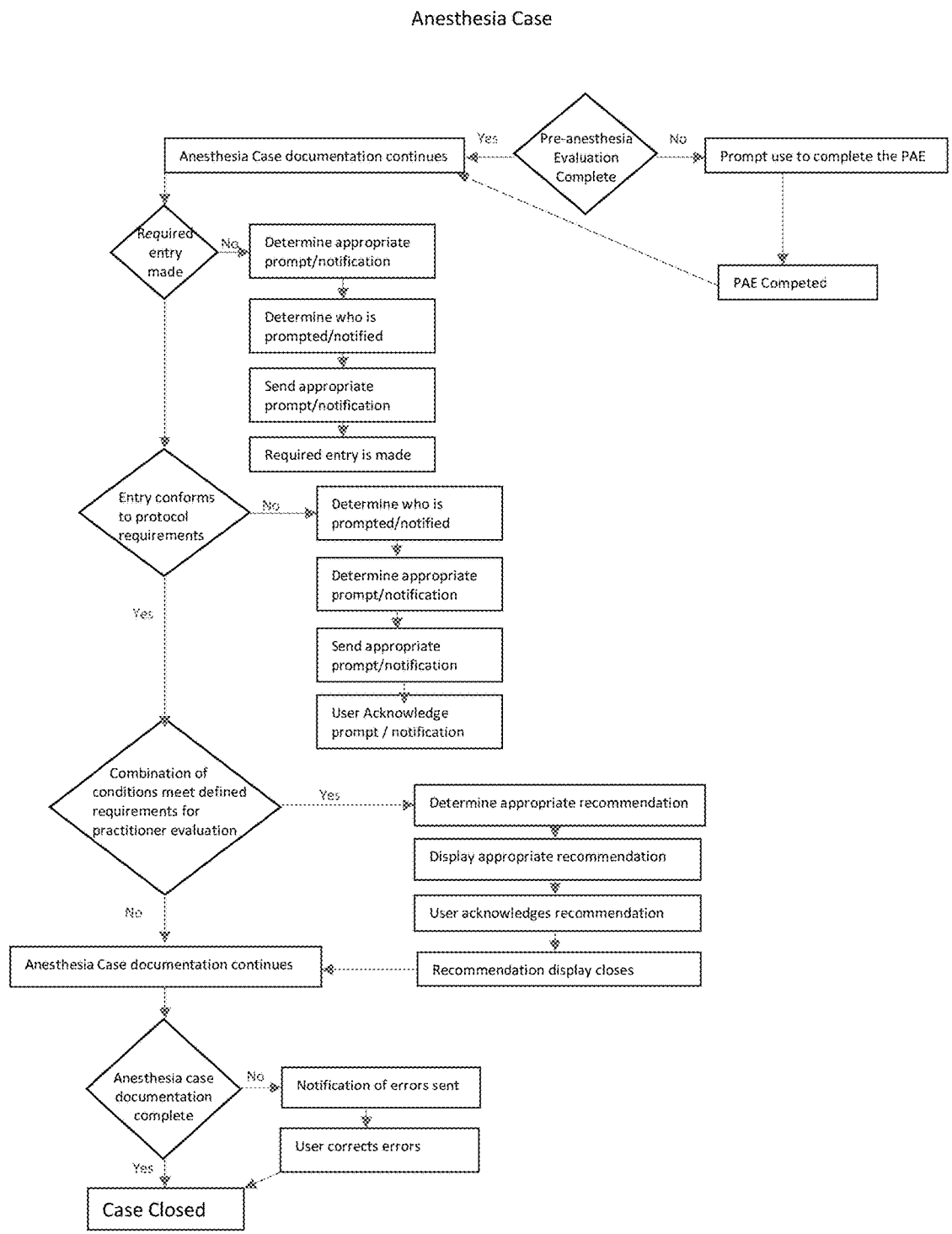
FIG. 13 is a flow diagram of an anesthesia case illustrating the continuous improvement system of the present invention.

As can be seen in FIG. 13, which is presented in the context of an anesthesia case documentation, once the pre-anesthesia evaluation is complete, the anesthesia case documentation continues. Determinations are made about prompt notification and who should be notified. Other determinations can be made and they will provide the reviewer guidance. The entry is evaluated by the user interface rules engine to evaluate against the defined requirements for practitioner evaluation. The result is the determination of appropriate recommendations, a display of the recommendations and an acknowledgement of the recommendations. If there are errors, a notification of errors is sent for the user to correct the errors. If there are no errors, the documentation is complete and the case is closed.

Documentation of patient plan provides a means to use the protocol template to define the facility patient care protocol requirements or to define a specific patient care plan within the facility protocol requirements. The notifications and prompts will support the patient care plan. Documentation of care allows the providers to enter manual data and see real time data on the protocol workflow screen. This screen provides a means to review real time automated documentation and enter data required to be entered manually and receive prompts, notification, or Clinical Decision Support suggestions.

Remote supervision and monitoring provide a means to see an overview of each care assigned to the individual. The user is provided the ability to access specific cases to see real time patient status as well as review data from earlier in the case. Review of specific cases provides the user with the ability to select a specific case for review. Access to the record provides the user with the ability to moved back and forth during the case to facilitate review of the case.

Creation of data search criteria provides a means to access search templates configured to specific protocols. These templates may be modified to include additional quality data not included in the Electronic Health Record (EHR). Access to search results provides a means to review the cases meeting the defined search criteria. For example, the continuous improvement tool utilizes the Creation of search criteria and access to search results. The user defines the search criteria by populating search templates configured similar to the workflow screens used during patient care protocols. The populated templates provide the search criteria for the search engine to retrieve the data, store the data for use access and review, and notification that the search results as defined by the user are available. Process steps include:

Embodiments of the present invention, including the user interface rules engine, can be implemented in digital electronic circuitry, or in computer hardware, firmware, software, or in combinations thereof. An apparatus can be implemented in a computer program product tangibly embodied or stored in a machine-readable storage device for execution by a programmable processor; and method actions can be performed by a programmable processor executing a program of instructions to perform functions by operating on input data and generating output. The embodiments described herein, and other embodiments of the invention, can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language.

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks, cloud servers. Computer readable media for embodying computer program instructions and data include all forms of non-volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in special purpose logic circuitry. Any of the foregoing can be supplemented by, or incorporated in, ASICs (application-specific integrated circuits).

To provide for interaction with a user, embodiments can be implemented on a computer having a display device, e.g., an LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of embodiments, or any combination of such back end, middleware, or front-end components. The components of the system can be interconnected by any form or medium of digital data communication, e.g., a communication network. Examples of communication networks include a local area network (LAN) and a wide area network (WAN), e.g., the Internet.

The system and method or parts thereof may use the "World Wide Web" (Web or WWW), which is that collection of servers on the Internet that utilize the Hypertext Transfer Protocol (HTTP). HTTP is a known application protocol that provides users access to resources, which may be information in different formats such as text, graphics, images, sound, video, Hypertext Markup Language (HTML), as well as programs. Upon specification of a link by the user, the client computer makes a TCP/IP request to a Web server and receives information, which may be another Web page that is formatted according to HTML. Users can also access other pages on the same or other servers by following instructions on the screen, entering certain data, or clicking on selected icons. It should also be noted that any type of selection device known to those skilled in the art, such as check boxes, drop-down boxes, and the like, may be used for embodiments using web pages to allow a user to select options for a given component. Servers run on a variety of platforms, including UNIX machines, although other platforms, such as Windows 2000/2003, Windows NT, Sun, Linux, and Macintosh may also be used. Computer users can view information available on servers or networks on the Web through the use of browsing software, such as Firefox, Netscape Navigator, Microsoft Internet Explorer, or Mosaic browsers. The computing system can include clients and servers. A client and server are generally remote from each other and typically interact through a communication network. The relationship of client and server arises by virtue of computer programs running on the respective computers and having a client-server relationship to each other.

The present invention provides continued care software that uses elements of the assessment data to provide decision support and that prompts a user for input to provide decision support to caregivers. A decision support algorithm responds to elements of assessment data to produce textural material describing a medical condition, scientific treatments and possible complications. This information is available in real time to assist in all types of clinical decisions from diagnosis to treatment to triage.

The system of the present invention collects the data, time stamps and stores the data. The patient record in the medical facility electronic health record system (EHR) contains the same information as is known in the art with other systems. The EHR is one target and receives only the data required by the specific target. The data sent to the EHR plus any other data collected is stored in the cloud and filed to support the assessment of the case. There is the ability to store some of the data as case record and other additional data collected in the Quality data. Thus, the present invention can add functionality and features by finding ways to more fully leverage the knowledge that is gained as the system gains knowledge. Thus, the system has the ability to grow as new knowledge is gained.

The invention is capable of collecting any identified data at a frequency that supports a meaningful assessment of patient interactions and patient response to those interactions. The term data includes but is not limited to patient medical history, patient interaction details including person performing the interaction, the time provided, any drug, disposable or medical device used to complete the interaction, alpha numeric patient vital signs provided by active patient monitors, Wave forms provided by active patient monitors, changes to settings of any medical device used on the patient, lab results, practitioner notes and documented observations.

The invention is capable of displaying the information along a timeline of the treatment period. The display may be configured to provide a graphical representation of any alpha numeric patient vital sign collected during the treatment. Additionally, the invention supports the viewing of the waveform data generated during the treatment as an accurate representation of the waveform screens on the active patient monitors.

Using the review screen, the user may select any specific time on the timeline to review the patient vital signs values at that time. With respect to alpha numeric and wave form data the system has the ability to move forward and backward during the treatment to assess potential link between patient interaction and patient response.

Using these tools, the person or team conducting the assessment may identify potential root causes and or potential corrective/preventive actions including the establishment of guidances. The system is designed to allow the user to establish parameter or conditional limits to implement guidances. In this case implement implies that the system will monitor future treatments (same treatment as reviewed) against specified conditions and when any of those conditions are observed, an alert/notification will be sent. The level of implementation may be limited to monitoring in the back ground without any interaction with the provider. In this case the individual(s) identified by the guidance will be notified that a treatment case of interest is available for review. Note: It is possible for several guidances to be created and implemented to accelerate the collection of data for various alternative approaches. Using this approach, the data necessary to build the required scientific evidence to justify the appropriate treatment protocol guidance may be collected without any change to currently approved protocols.

Once the scientific evidence has been collected to justify a formal change to the Medical Facility's protocol, the appropriate review can be performed and if adequately justified, approved for implementation via changes to the authorized protocol. As knowledge is gained using this basic design of experiment methodology using real-world data previously collected, sufficient logic may be developed to support the use of machine learning tools to further accelerate the continuous improvement program.

The present invention supports the ability to move back in time during the current patient care under review. The same screens may also be utilized to evaluate the case during formal reviews. These screens also include icons to show when specific patient interactions were performed.

The waveform data is collected directly from the medical devices. These wave forms are stored with the patient records and as quality data. Once stored the waveforms may be displayed and played. With the ability to play the stored wave forms the system is also includes to play, replay, fast forward or fast reverse to identify the time periods of most interest to the medical practitioner reviewing these records.

Improved patient outcome requires a continuous spiral of improved process control. Therefore, continuous improvement programs focus on patient outcome and identifying opportunities to eliminate unexpected outcomes. The narrowly focused quality improvement programs look for situations where the existing process controls or procedures yield negative outcomes. Truly advanced programs also look for situations where the outcomes are more positive than expected. When situations presenting opportunities for improvement are identified, the organization determines the risk of a repeat event and prioritizes resources to address the top opportunities. The identified situations are tracked and managed in the Corrective and Preventive Action (C/APA) process. This process requires documented Failure Investigation details, assessment of potential corrective and/or preventive actions, verification and validation outcomes of the CAPA actions tried.

As discussed above, the current prior art systems do not adequately support an effective Continuous Improvement Program.

The present invention as previously discussed provides the means to support a Quality Improvement Program focused on the:
   i. elimination of preventable events
   ii. improvement of patient care protocol compliance
   iii. advance failure investigation tools
   iv. user friendly data searches
   v. advance use of real-world data with unlimited data storage and data access to support any number of study types, including real-world data based clinical studies.
   vi. etc.

Example of a User Accessing the Continuous Improvement Tool

The User selects the desired patient care protocol template.

The template is familiar to the user because it is similar to the patient care plan and patient care protocol workflow screens.

The User populates the template with the desire search criteria including but not limited to the following:

| Patient medical identifiers |
| --- |
| Age |
| Sex |
| Socio-economic details |
| Blood type |
| Drug/Alcohol/smoking history |
| Patient care interactions |

-continued

| Patient medical identifiers |
|---|
| Medication delivery |
| Medical Device settings |
| Incision |
| Ventilation |
| Medical device setting changes |
| Blood delivery |
| Patient response |
| Vital signs |
| Alpha numeric data |
| Wave forms |
| Images |
| Test results |
| Blood interactions |
| Patient care team members |
| # of transfer of care events during treatment |
| Patient care location such as operating room 1 |
| Treatment time such time of day, day of week, etc. |
| Time interval of cases to be evaluated |
| Planned Notification of results, who, when and method of notification |
| The User reviews and accepts the search request. |

The continuous improvement engine reviews stored data from cases within the defined time interval against the defined search criteria.

The User is notified that the search request is completed.

Once the search is completed historic data and applicable cases are available for review. If the search request included current and/or future active cases the user may be notified when the defined criteria is observed during the case. In this case the user may request real time notification of the identified cases and/or delayed notification of these cases. The User and/or the review team reviews and analyzes the results of the search to determine the validity of their hypothesis. Modification to populated search template may be accomplished by editing specific details. For advanced retrospective studies, the process identified above may be repeated for the identified variations required in the study. Finally, the User executes a rules engine against contents of electronic medical records (or EMRs) to determine whether the EMRs comply with one or more governmental regulations. These rules are applied and all required patient care documentation must be present prior to closure of the case.

The system of the present invention will best be used when there is a specific reason to analyze the details of the case of interest and other similar cases. For example, in response to a Sentinel or Never event. However, the tool can be used for detailed analysis of any historical data. As customer knowledge is gained by using various analytical tools, the tool can be expanded to assess historical records which meet the criteria selected for review. This historical review may be used to collect data supporting the required scientific justification to validate any proposed change.

FIG. 1 is a flow diagram which shows the continuous improvement tool utilization logic and process of the present invention. It begins by identifying the case of interest, accessing the case, and reviewing the case to identify items or periods of interest. After an iterative process of analysis, guidance rules are created and applied to cases of interest, including notifications and communications about protocol changes and implementation.

Figure 2:
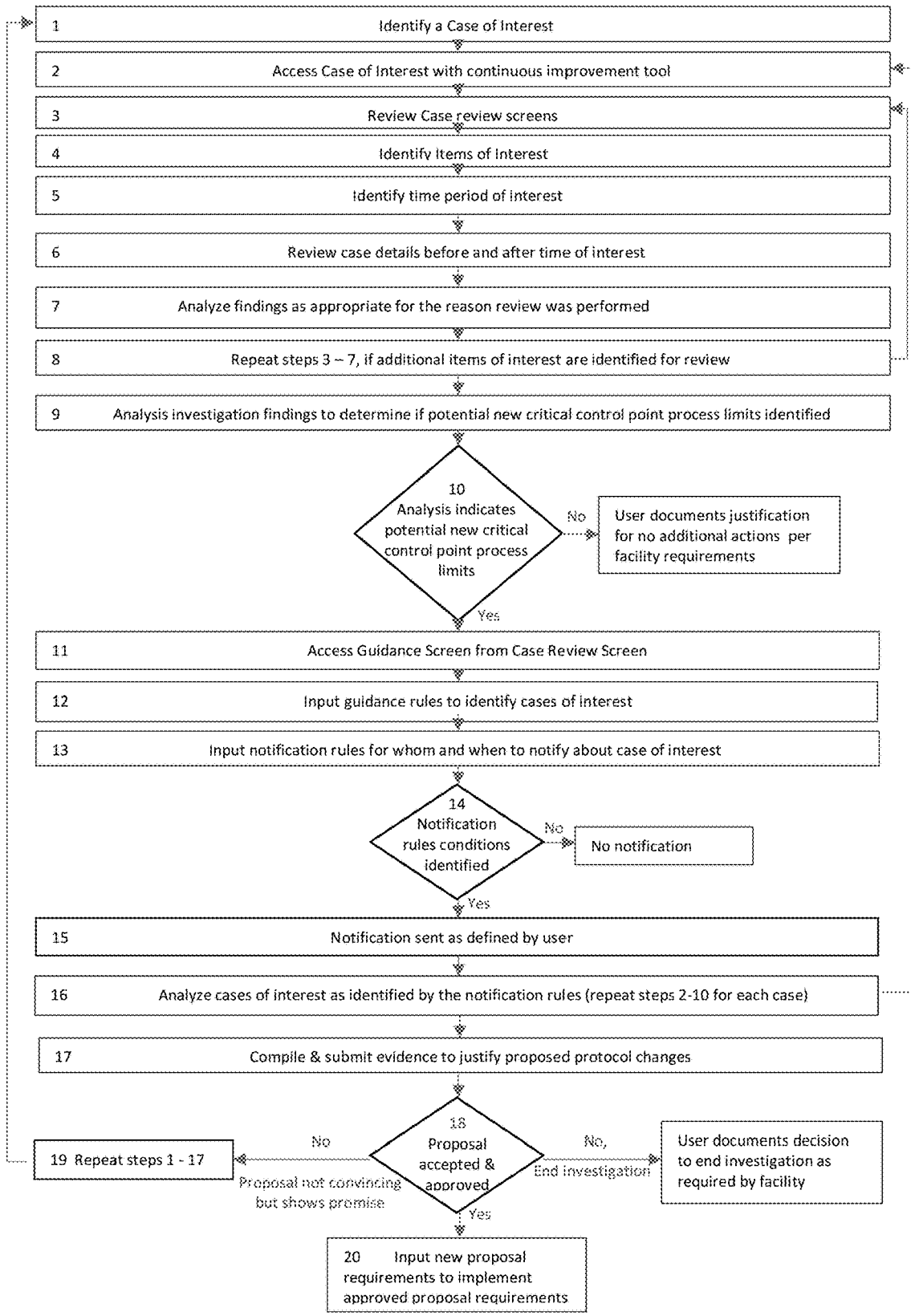
FIG. 2 is a flow diagram of the use of the continuous improvement system of the present invention.

FIG. 2 is a flow diagram of the use of the continuous improvement system of the present invention. The use could, for example, be the use for an anesthesia protocol illustrated in FIGS. 3-10. In that process, a case is identified and accessed. The case is reviewed while identifying items and time periods of interest to determine the document findings and analysis. If the analysis indicates potential new critical control points in the process limits, the user can create guidance rules to identify cases of interest and the notification rules can be implemented. If further cases of interest are identified, then further review is warranted. If no further review is warranted, then the evidence is compiled and submitted to justify protocol proposals, which are then submitted for approval.

FIGS. 3-10 provide an example for an anesthesia protocol. However, the example and its slides and explanation of each screen are not intended to limit the scope of the capabilities of the Continuous Improvement Tool. The tool may be configured to support any number of processes.

Figure 3:
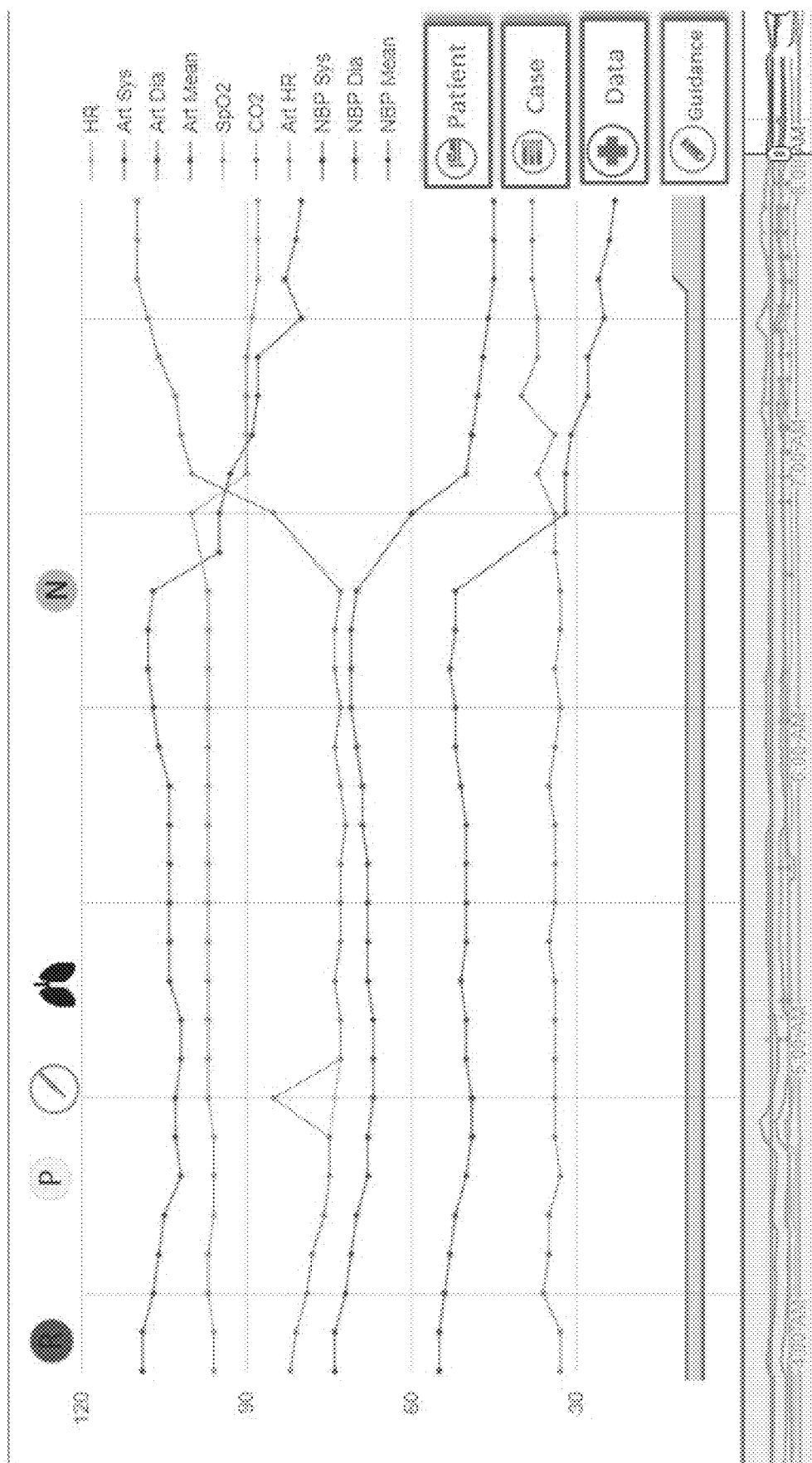
FIG. 3 is a screen shot showing a case analysis review screen.
Figure 4:
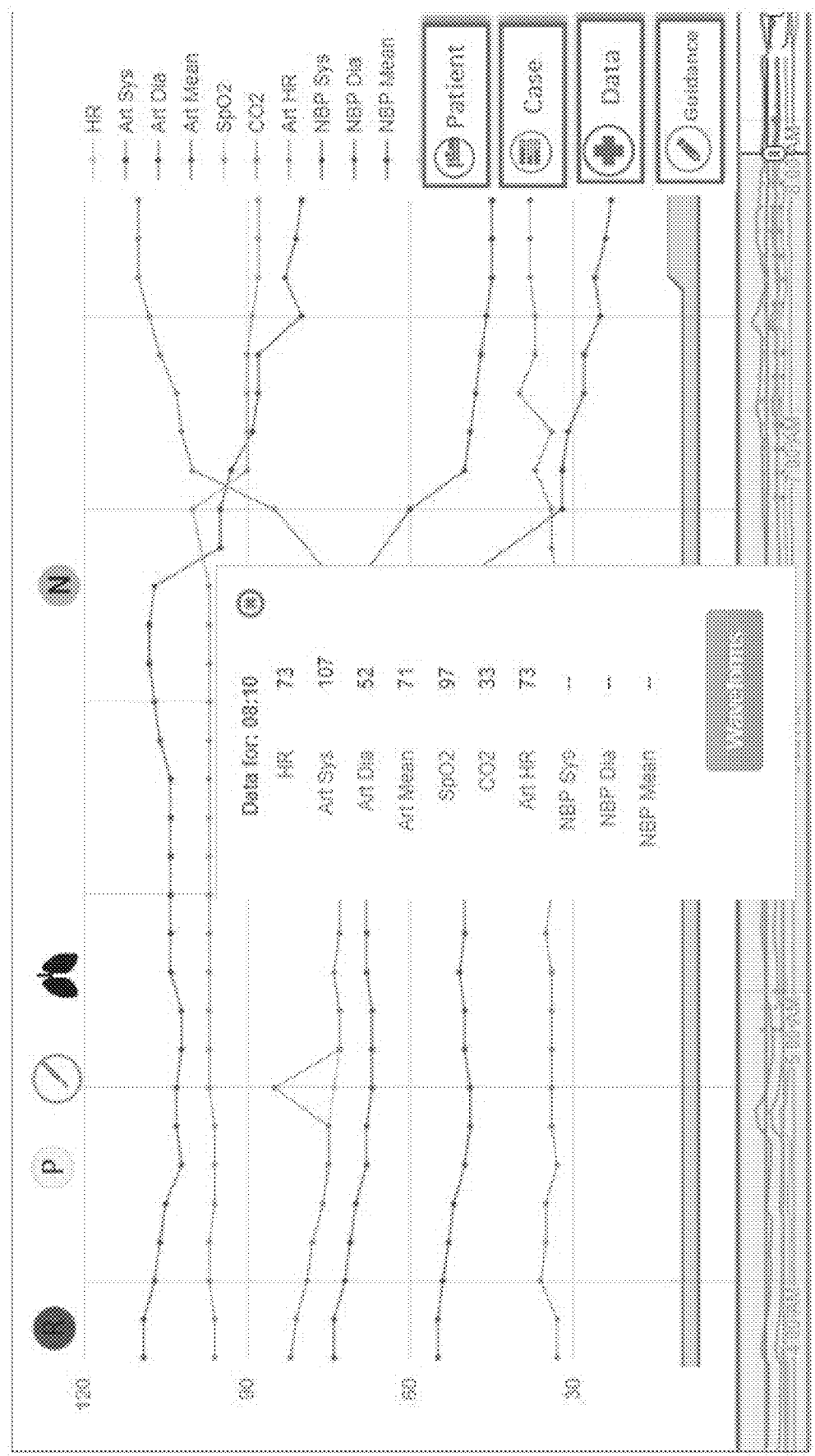
FIG. 4 is a screen shot showing a case analysis review screen showing interaction with data options.
Figure 5:
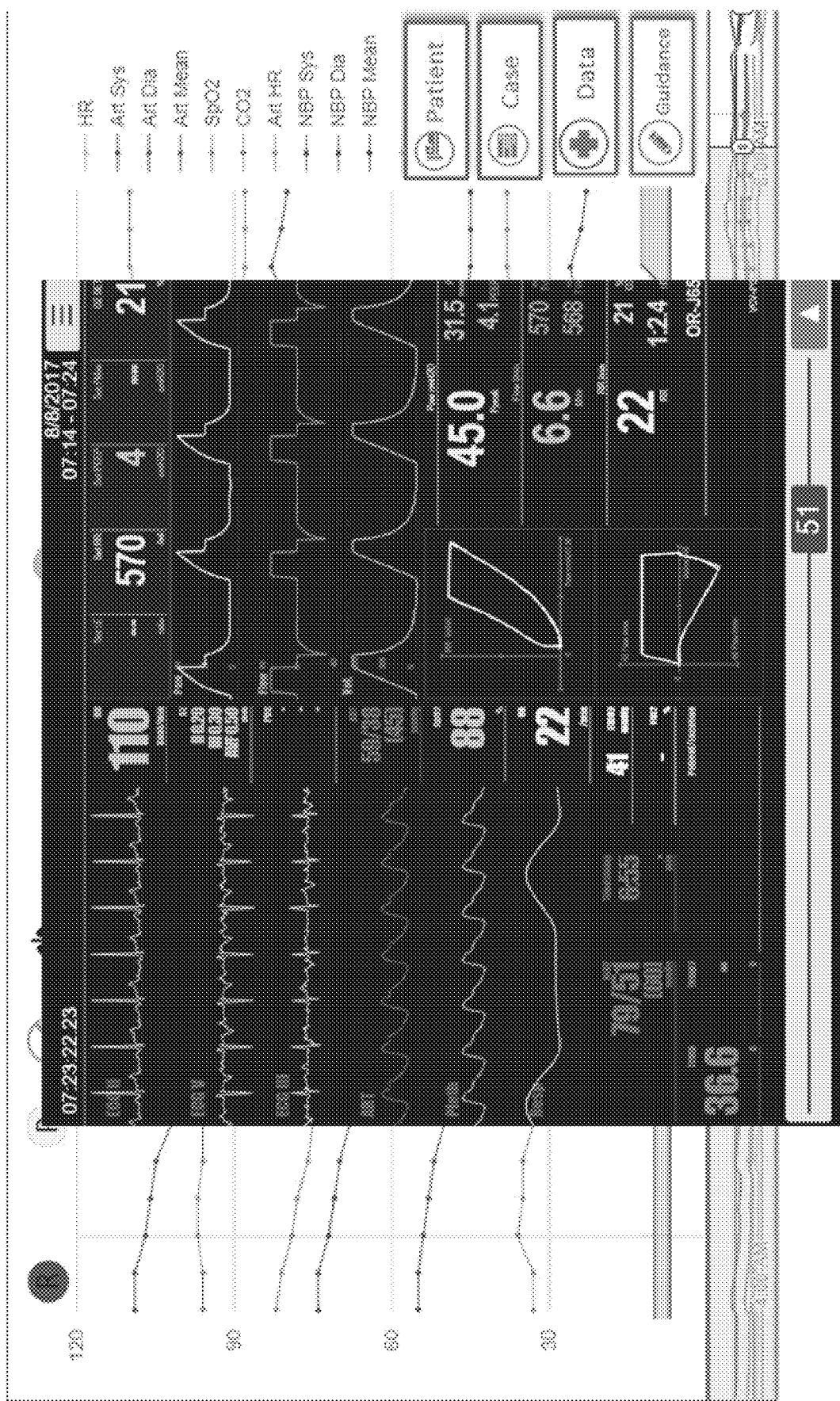
FIG. 5 is a screen shot showing a case analysis review screen which includes waveform displays.

In the present example of a case analysis, a review screen is provided that provides on overview of the case including, but not limited to:
  Graphical representation of the patient vital signs during the case, including icons indicating when specific interaction with patient occur
  Legend of the graphs
  Drug delivery
  Incision
  Ventilation
  Case Detail Selection Keys
  Patient—details
  Case
  Data
  Guidance The screenshots provide a walk-through of an example where data collected through a case is reviewed. In the timeline, data from multiple sources is visible along with clinical events, (i.e. incision) The screenshots, FIGS. 3, 4, and 5 show how clinicians interactively review data along with the guidance editor. Then can evaluate their current process controls (FIG. 6) and make changes to processes based on the review of the case. The screenshots show an example of how this happens. For example, during a review, clinicians might identify that the data showed in the screens of the review tool might be more effective if it also showed data from available, from cerebral oximetry. Because the platform supports Cerebral monitors, clinicians can request to include cerebral oximeters in the data set collected, so that clinicians can review and use its data to create more effective guidance.

FIG. 3 is a screen shot of a review screen showing an interaction with the review screen data options, including an ability to move the cursor to a specific time in the case and clicks to see specific data details. This screen shot displays the actual collected data at the requested time of the case in the screen shot in FIG. 4.

To see waveforms the user clicks on the waveform key, as shown in the screen shot in FIG. 3 and the waveform data collected is displayed as shown in the screen shot in FIG. 5

Figure 6:
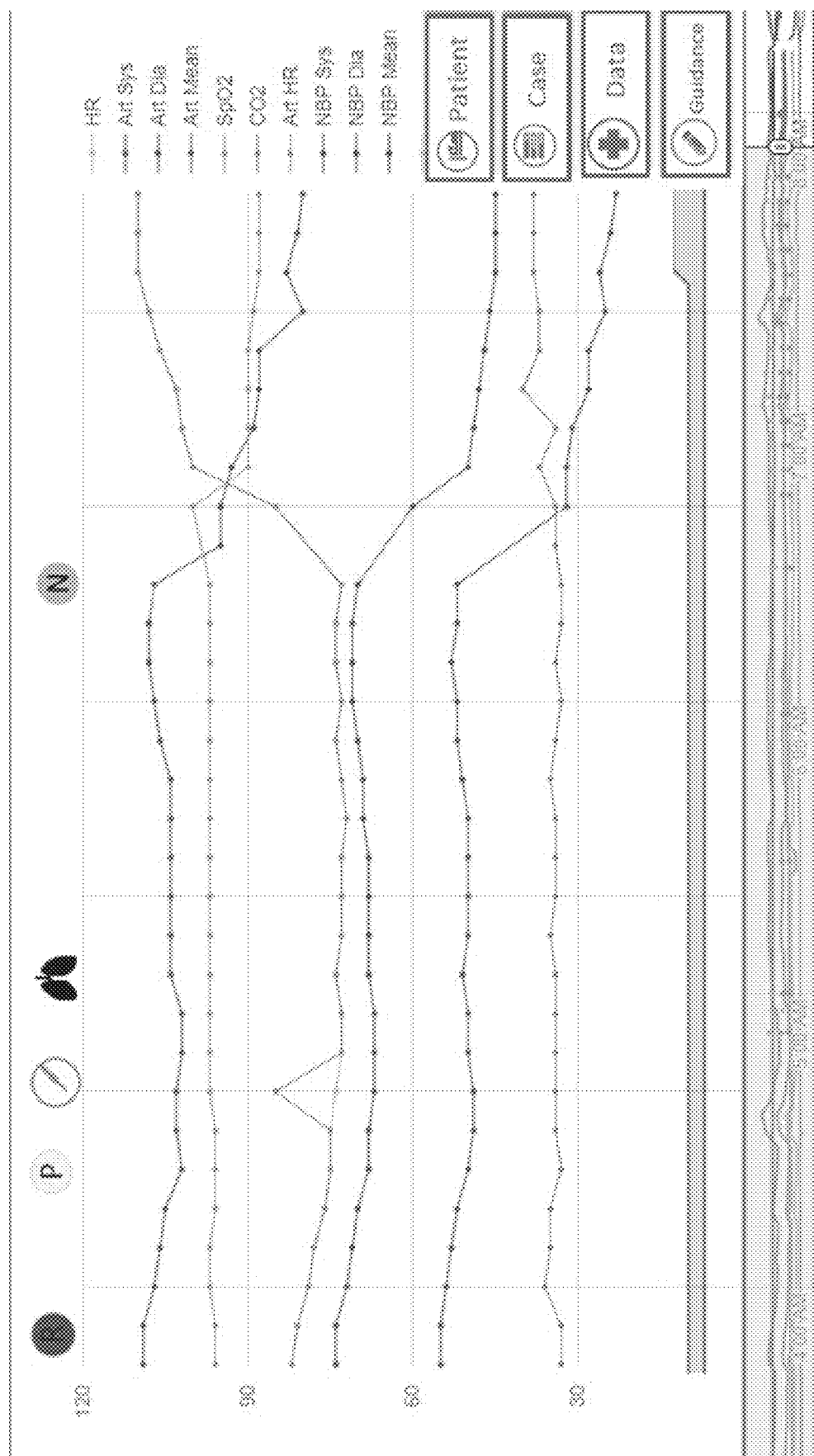
FIG. 6 is a screen shot showing a case analysis review screen showing a guidance tool to create or modify a guidance.

As seen in the screen shot is FIG. 6, there is a slide at the bottom of the waveform display, which enables the user to move the time back or forward to review changes before or after the selected time.

The screen shots illustrate how, from the review screen the user can access the guidance tool which walks the user through the process to create or modify a guidance.

Figure 7:
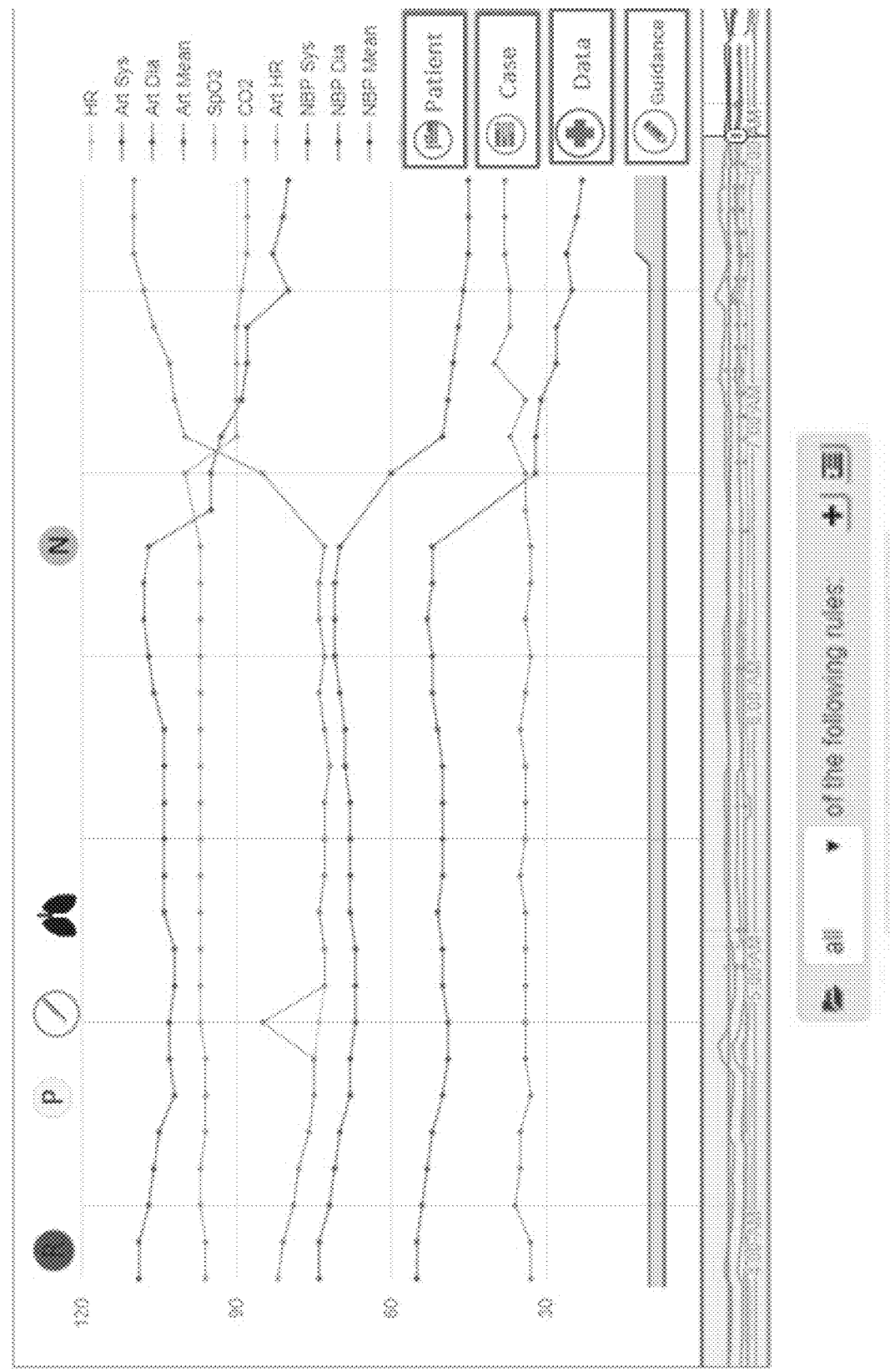
FIG. 7 is a screen shot showing a case analysis review screen showing the selection of a primary filter.

FIG. 7 shows the review screen and the selection of the scope of the primary filter which in this case defines the case type a GENA.

Figure 8:
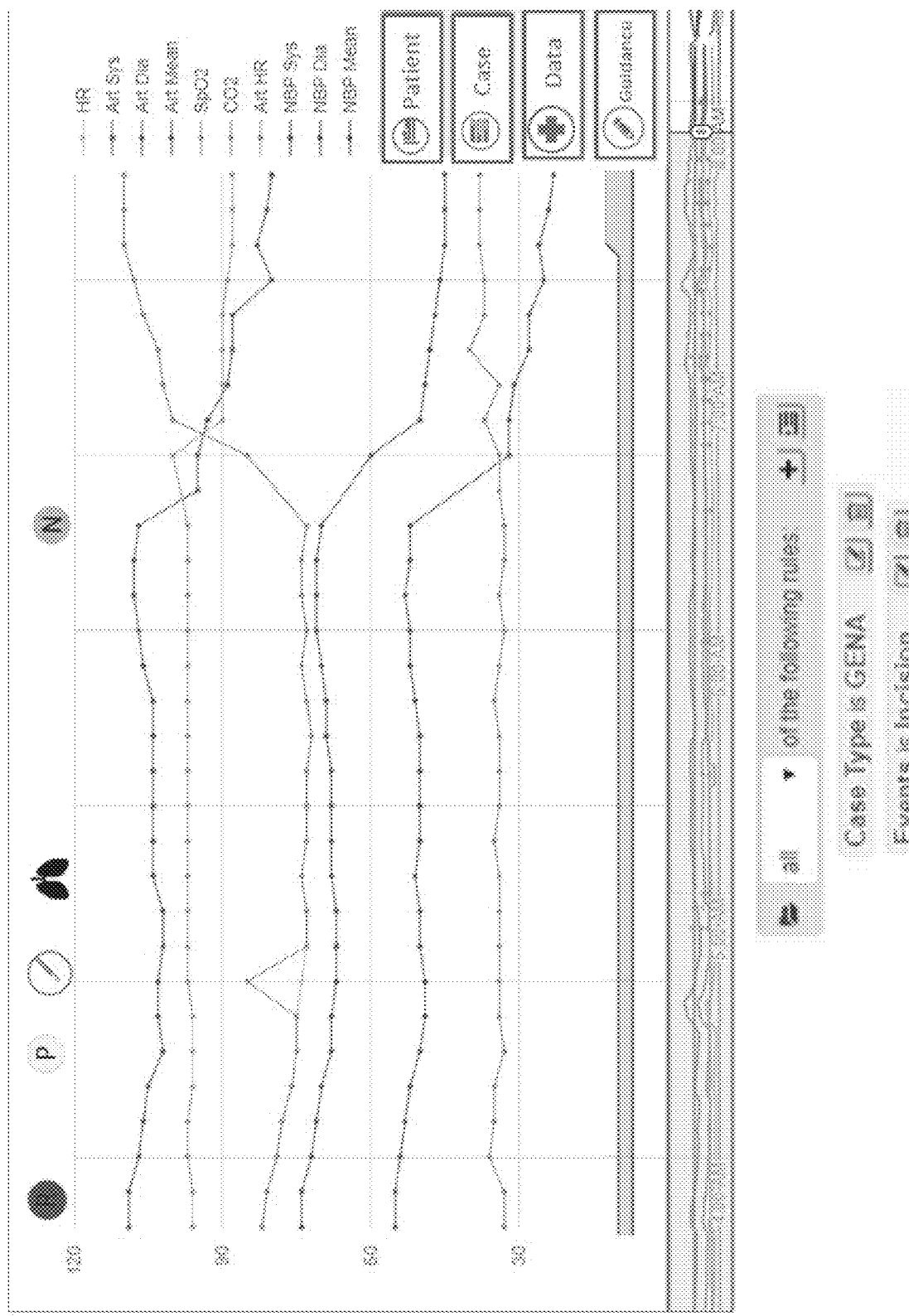
FIG. 8 is a screen shot showing a case analysis review screen indicating that the event is an incision.

FIG. 8 shows the review screen and patient interactions, as well as showing that the event is an incision.

Figure 9:
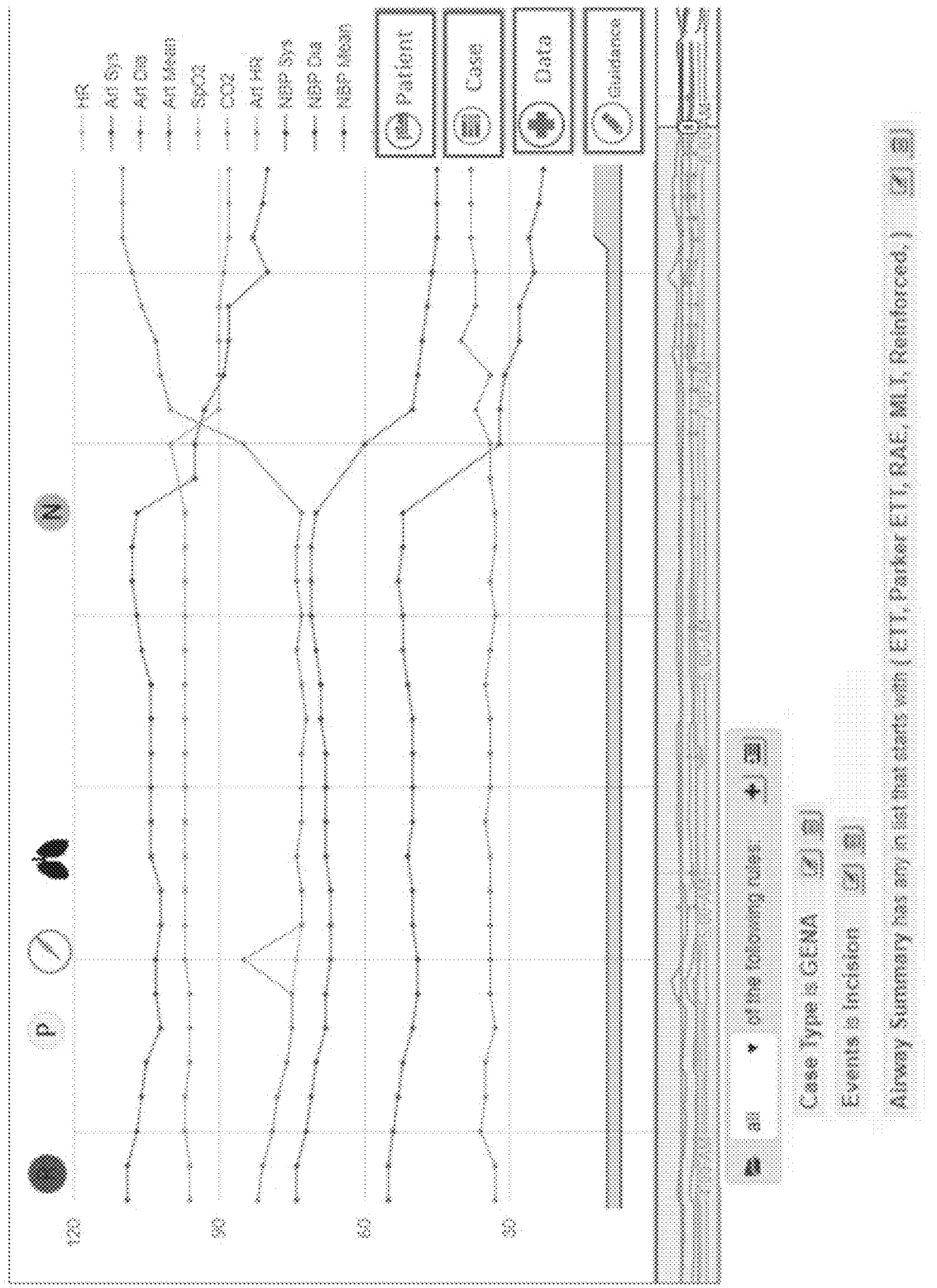
FIG. 9 is a screen shot showing a case analysis review screen which provides an airway summary.

FIG. 9 shows a screen shot of an airway summary and has any list that starts with ETT, Parker ETT, RAE, MLT and/or reinforced.

Figure 10:
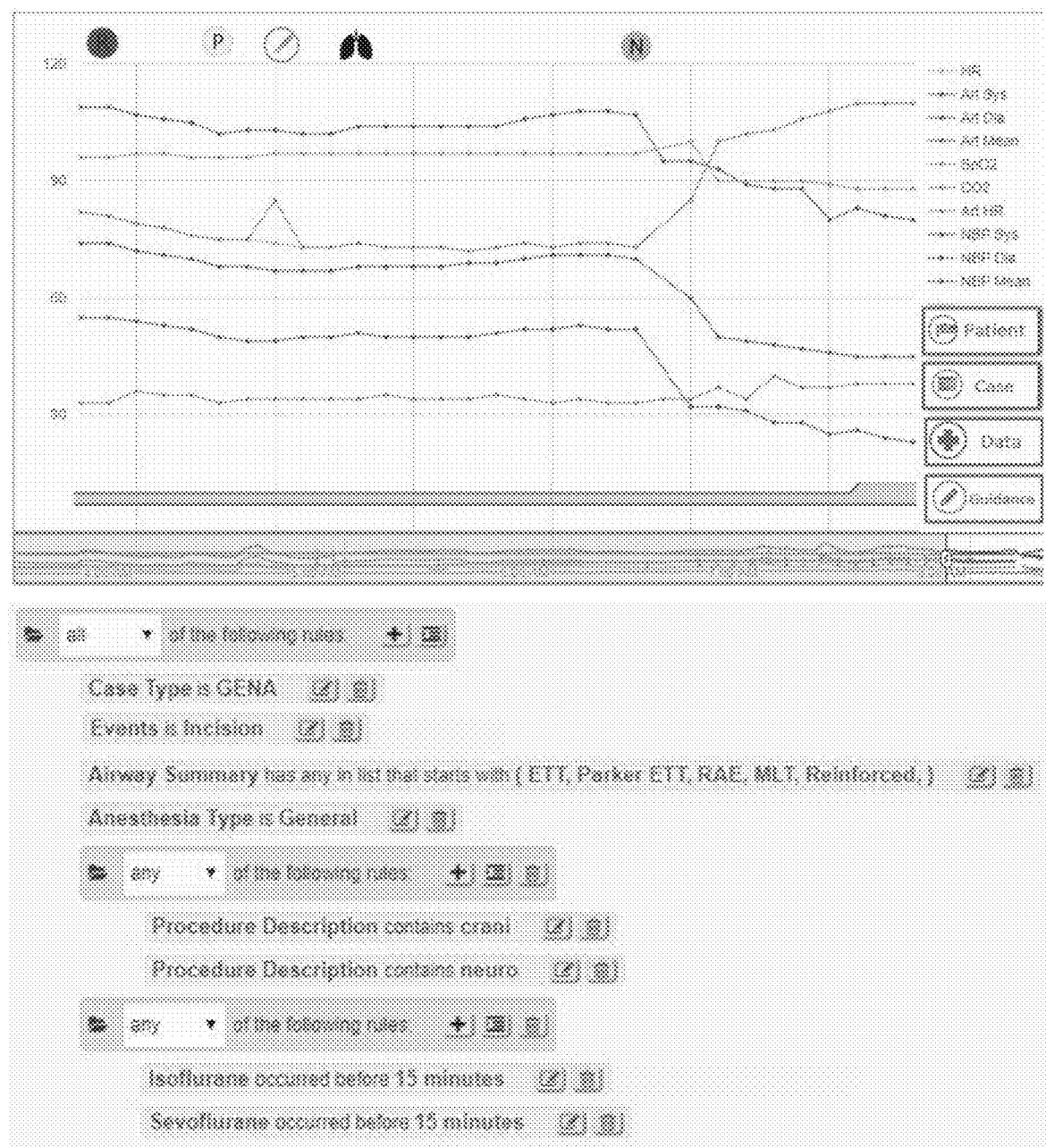
FIG. 10 is a screen shot showing a case analysis review screen showing that the anesthesia is general, as well as the secondary and third level filters.

FIG. 10 shows a screen shot indicating that the anesthesia type is general and defines the scope of secondary filter according to certain rules, including whether the procedure description contains crani and/or the procedure description contains neuro. FIG. 10 also shows the definition of the 3rd level filter, and indicates that Isoflurane occurred before 15 minutes and Sevoflurane occurred before 15 minutes.

Figure 11:
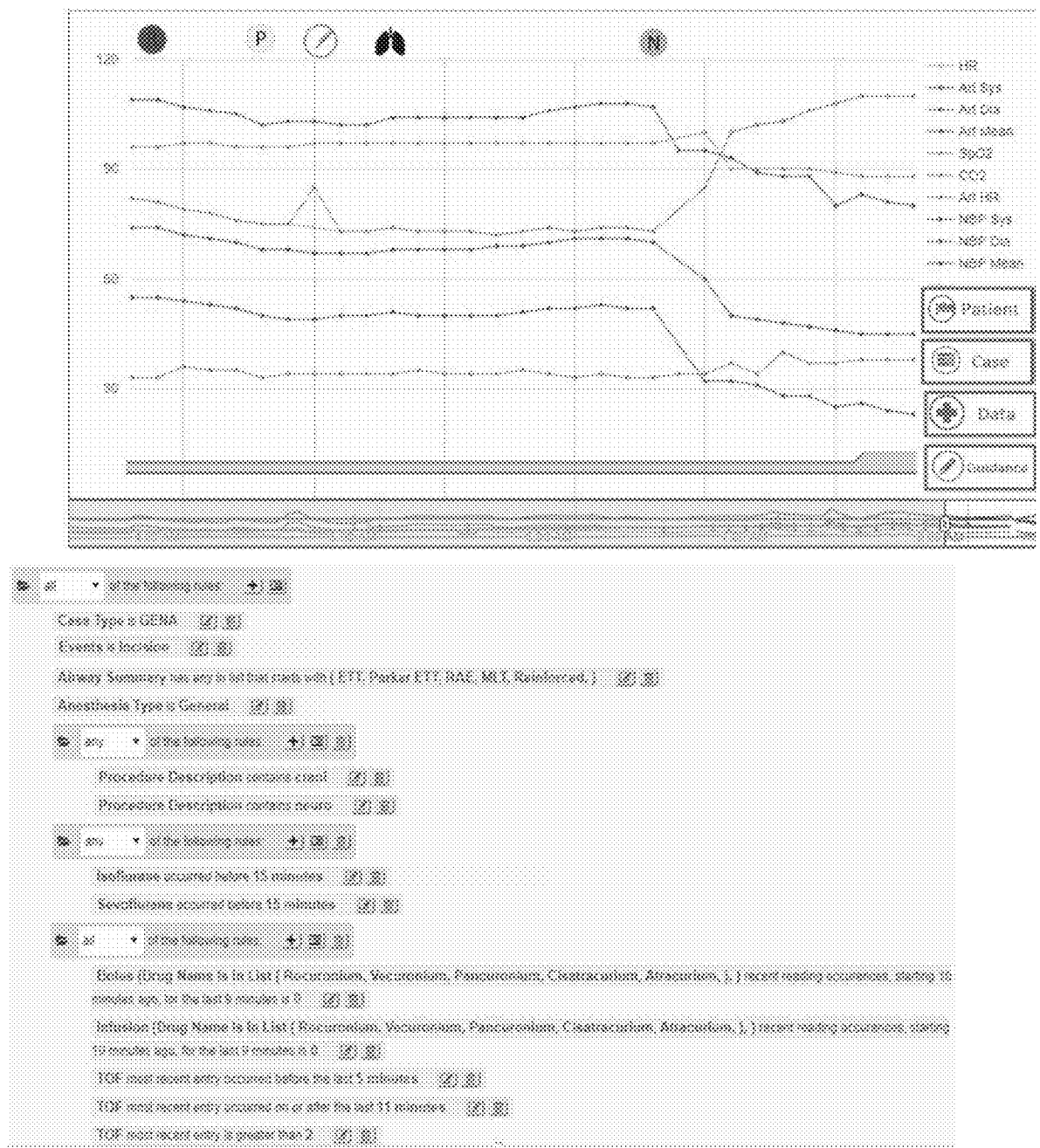
FIG. 11 is a screen shot showing a case analysis review screen which defines the scope of the fourth level filter.

FIG. 11 shows the scope of a 4th level filter as defined by the following rules;

Bolus (Drug Name is in List (Rocuronium, Vecuronium, Pancuronium, Atracurium)) recent reading occurrences starting 10 minutes ago for the last 9 minutes is 0

Infusion (Drug Name is in List (Rocuronium, Vecuronium, Pancuronium, Atracurium)) recent reading occurrences starting 10 minutes ago for the last 9 minutes is 0

TOF most recent entry occurred before the last 5 minutes

TOF most recent entry occurred on or after the last 11 minutes

TOF most recent entry is greater than 2

The foregoing embodiments of the present invention have been presented for the purposes of illustration and description. These descriptions and embodiments are not intended to be exhaustive or to limit the invention to the precise form disclosed, and obviously many modifications and variations are possible in light of the above disclosure. The embodiments were chosen and described in order to best explain the principle of the invention and its practical applications to thereby enable others skilled in the art to best utilize the invention in its various embodiments and with various modifications as are suited to the particular use contemplated.

What is claimed is:

1. A system for handling data, comprising:
a communication hub configured to couple to a plurality of electronic devices via a communications network, the communication hub being configured to receive, in real time, data from the electronic devices, the data from the electronic devices acquired in real time, and to process the data received from the electronic devices in real time, the processing including generating time stamped data based on the data received from the electronic devices, synchronizing the time stamped data to provide a standardized time basis for presentation, translating the time stamped data to a first machine-language, and translating a portion of the time stamped data to be sent to a receiving one of the electronic devices from the first machine-language to a second language determined by the communication hub to be compatible with the receiving electronic device;
a data storage device configured to couple to the communication hub via the communication network and storing the time stamped data in one or more records, each of the records relating to a corresponding one of the patients, wherein the time stamped data includes medical condition data, history data, status data, and monitored elements data and wherein each record includes the medical condition data, the history data, the status data, and the monitored elements data received from corresponding ones of the electronic devices that relates to the corresponding one of the patients; and
a user interface rules engine configured to couple to the communication hub via the communication network and implemented in a computer program product tangibly embodied or stored in a non-transitory machine-readable storage device for execution by a programmable processor, the user interface rules engine permitting a user to define protocol requirements dictating conditions required for updating the records, the user interface rules engine configured to receive the time stamped data in real time and process the time stamped data in realtime, including processing the time stamped data in real time in order to display the time stamped data stored in a record corresponding to a selected one of the patients of the data storage device organized per the user defined protocol requirements within a timeline of events over a patient treatment time span based on the standardized time basis, the user interface rules engine being configured to display, for the selected one of the patients, the time stamped data regarding treatment at a selected time and selected portions of the time stamped data from the record corresponding to the selected one of the patients at a time of the patient treatment time span before or after the selected time, the protocol requirements including a required sequence of patient care procedure steps.

2. The system of claim 1, wherein, upon occurrence of a predetermined event in regard to the selected one of the patients, the user interface rules engine is configured to gather from the data storage device, the time stamped data corresponding to the selected one of the patients for a first predetermined time before and a second predetermined time after the predetermined event to generate the timeline of events.

3. The system of claim 2, wherein the predetermined event is detected by the user interface rules engine based on the record corresponding to the first patient.

4. The system of claim 2, wherein the predetermined event is indicated to the user interface rules engine by the user via the user interface.

5. The system of claim 1, wherein the communication hub is configured to send the portion of the time stamped data in the second language to the receiving electronic device.

6. The system of claim 1, wherein the user interface rules engine is configured to permit the user to define user-defined criteria determining when the user interface rules engine will communicate that cases meeting the user-defined criteria are available for review.

7. The system of claim 1, wherein the user interface rules engine is configured to display a graphical representation of any alpha numeric patient vital sign generated during the patient treatment time span and waveform data generated during the patient treatment timespan.

8. The system of claim 1, further comprising: a guided template builder providing to the user a plurality of configuration templates, each of which is specific to a corresponding patient care protocol, the templates being configured to be populated with a search criteria and to receive from the user a time period for which the time stamped data is to be retrieved in response to a search,
wherein the guided template builder retrieves the time stamped data from the records and/or quality data collected during patient care encounters.

9. The system of claim 1, wherein the system identifies actionable data using an algorithm based on user defined criteria.

10. The system of claim 1, wherein the user interface rules engine is further configured to display, with the timeline of events, a notification rules generator via which a user can set one or more filters for defining specific notification rules to define when to provide notification when a defined condition is met, the notification rules generator including one or more menus, each menu associated with a respective filter of the one or more filters, the notification rules generator displaying one or more user-defined rules for each filter, and each menu including an all selection and an any selection, the all selection dictating that all user-defined rules for that filter be met and the any selection dictating that any of the user-defined rules for that filter be met.

* * * * *